United States Patent
Ishihara et al.

(10) Patent No.: US 9,962,319 B2
(45) Date of Patent: May 8, 2018

(54) ONE-COMPONENT-TYPE DENTINAL TUBULE SEALANT

(71) Applicant: KURARAY NORITAKE DENTAL INC., Kurashiki-shi (JP)

(72) Inventors: Shumei Ishihara, Tainai (JP); Kenji Hatanaka, Tainai (JP)

(73) Assignee: KURARAY NORITAKE DENTAL INC., Kurashiki-shi (JP)

( * ) Notice: Subject to any disclaimer, the term of this patent is extended or adjusted under 35 U.S.C. 154(b) by 0 days. days.

(21) Appl. No.: 15/024,530

(22) PCT Filed: Sep. 29, 2014

(86) PCT No.: PCT/JP2014/075822
§ 371 (c)(1),
(2) Date: Mar. 24, 2016

(87) PCT Pub. No.: WO2015/046491
PCT Pub. Date: Apr. 2, 2015

(65) Prior Publication Data
US 2016/0228336 A1    Aug. 11, 2016

(30) Foreign Application Priority Data

Sep. 30, 2013  (JP) ................................. 2013-205010

(51) Int. Cl.
| | |
|---|---|
| *A61K 6/033* | (2006.01) |
| *A61K 6/00* | (2006.01) |
| *A61K 6/02* | (2006.01) |
| *A61K 8/24* | (2006.01) |
| *A61Q 11/00* | (2006.01) |
| *A61K 8/34* | (2006.01) |
| *A61K 8/86* | (2006.01) |
| *A61K 8/02* | (2006.01) |
| *A61K 8/19* | (2006.01) |

(52) U.S. Cl.
CPC ............ *A61K 6/033* (2013.01); *A61K 6/0008* (2013.01); *A61K 6/0017* (2013.01); *A61K 6/02* (2013.01); *A61K 8/0241* (2013.01); *A61K 8/19* (2013.01); *A61K 8/24* (2013.01); *A61K 8/345* (2013.01); *A61K 8/86* (2013.01); *A61Q 11/00* (2013.01); *A61K 2800/412* (2013.01); *A61K 2800/413* (2013.01); *A61K 2800/5922* (2013.01); *A61K 2800/651* (2013.01)

(58) Field of Classification Search
CPC ........ A61K 6/033; A61K 6/0017; A61K 6/02; A61K 6/0008; A61K 8/24; A61K 8/345; A61K 8/86; A61K 8/0241; A61K 8/19; A61K 2800/412; A61K 2800/413; A61K 2800/5922; A61K 2800/651; A61Q 11/00
See application file for complete search history.

(56) References Cited

U.S. PATENT DOCUMENTS

| | | | |
|---|---|---|---|
| 2009/0186090 A1* | 7/2009 | Zaidel ..................... | A61K 8/25 424/489 |
| 2010/0129298 A1* | 5/2010 | Sakuma .................. | A61K 8/24 424/57 |
| 2011/0104644 A1 | 5/2011 | Primus et al. | |
| 2012/0027829 A1 | 2/2012 | Hashimoto et al. | |
| 2013/0189337 A1* | 7/2013 | Hashimoto .......... | A61K 6/0017 424/401 |
| 2013/0251767 A1 | 9/2013 | Hashimoto et al. | |
| 2013/0266915 A1 | 10/2013 | Tsuruta et al. | |

FOREIGN PATENT DOCUMENTS

| | | | |
|---|---|---|---|
| JP | 10-17449 A | 1/1998 | |
| JP | 2005-325102 A | 11/2005 | |
| JP | 2013-71917 A | 4/2013 | |
| JP | 2013-82702 A | 5/2013 | |
| WO | WO 00/03747 | 1/2000 | |
| WO | 2010/113800 A1 | 10/2010 | |
| WO | WO-2010120003 A1 * | 10/2010 | ............... A61K 8/24 |
| WO | 2012/046667 A1 | 4/2012 | |
| WO | WO2012/046667 * | 4/2012 | ............. A61K 6/033 |

OTHER PUBLICATIONS

WO-2010120003 Machine Translation (Year: 2010).*
International Search Report dated Dec. 22, 2014 in PCT/JP2014/075822 filed on Sep. 29, 2014.
Extended European Search Report dated Apr. 25, 2017, in EP Application No. 14648283.9.

* cited by examiner

*Primary Examiner* — Sean M Basquill
(74) *Attorney, Agent, or Firm* — Oblon, McClelland, Maier & Neustadt, L.L.P.

(57) ABSTRACT

A dentinal tubule sealant including apatite particles (A) having an average particle diameter of 500 nm or less, a filler (B) having an average particle diameter of 1 to 10 μm, and a dispersant (C), wherein the weight ratio (A/B) of the apatite particles (A) to the filler (B) is 0.05 to 15, the dentinal tubule sealant contains 15 to 95 parts by weight of the dispersant (C) relative to 100 parts by weight in total of the apatite particles (A) and the filler (B), and the total amount of the apatite particles (A), the filler (B), and the dispersant (C) is 85 parts by weight or more relative to 100 parts by weight of the dentinal tubule sealant. There is thereby provided a dentinal tubule sealant excelling in dentinal tubule sealability immediately after treatment, durability of dentinal tubule sealing, ease of operation, and storage stability.

20 Claims, No Drawings

ONE-COMPONENT-TYPE DENTINAL TUBULE SEALANT

TECHNICAL FIELD

The present invention relates to a dentinal tubule sealant superior to conventional dentinal tubule sealants in dentinal tubule sealability immediately after treatment, durability of dentinal tubule sealing, ease of operation, and storage stability.

BACKGROUND ART

When eating cold food or hot food, sweet food or acidulous food, a severe electrifying pain of teeth is believed to be caused by stimulating the dentinal nerves of teeth. The dentin of teeth is penetrated by many dentinal tubules, and the inside of the dentinal tubules is filled with tissue fluid. The pain of teeth is believed to be caused, when the dentin is exposed, by stimulation of sensory nerves existing near the boundary between the dental pulp and the dentin induced by forced movement of tissue fluid in dentinal tubules upon receipt of an external stimulus. This stimulus is caused by anything that makes tissue fluid in a dentinal tubule move, and thus a mechanical or thermal stimulus and a stimulus including sweetness, acidity or that causes change in osmotic pressure cause a pain of the dentin. Therefore, a pain is induced by eating or drinking, brushing with a tooth brush, or exercise and hinders daily life severely. Dentinal hyperesthesia includes cervical hyperesthesia following tooth wear caused by improper brushing with a tooth brush or a defect on enamel or cement caused by tooth caries or the like, and hyperesthesia of a root surface caused by gingival recession or the like induced by wrong brushing. Due to recent aging of the population or recent increasing movement to preserve vital teeth, dentinal hyperesthesia caused by gingival recession or tooth root exposure tends to increase.

Many of the remedies currently applied to dentine hyperesthesia aim to arrest the movement of tissue fluid in dentinal tubules. Examples of methods for blocking external stimuli by various materials include (1) a method of mechanically covering an exposed dentin surface with a resin material or glass ionomer cement, (2) a method of sealing tubules with a product capable of reacting with calcium in the dentin using oxalic acid, and (3) a method of sealing tubules by clotting protein contained in tubules with glutaraldehyde.

However, the above-mentioned prior techniques are problematic in that the techniques do not allow reliable treatment for subgingival parts or interdental gaps because of low pH or high toxicity of materials. Moreover, there is a problem that dentinal tubule sealing is not maintained well in oral environments and the effect does not last. In order to solve these problems, the following techniques using calcium phosphate have recently been disclosed.

Patent Document 1 discloses a composition for hyperesthesia capable of preventing or treating dentinal hyperesthesia by use of particles of hydroxyapatite or tricalcium phosphate having a particle diameter of 1.0 µm to 5.0 µm. However, the composition is problematic in that dentinal tubules cannot be sealed densely thereby and durable dentinal tubule sealing cannot be obtained therefrom because calcium phosphate having a particle diameter of 1.0 µm to 5.0 µm unfavorably forms gaps between particles immediately after physically entering into dentinal tubules having a diameter of 2 to 3 µm.

Patent Document 2 discloses a dentinal tubule sealant containing calcium phosphate particles as small as 900 nm or less. According to this document, calcium phosphate particles filled in dentinal tubules function as a nucleus after being surely filled into the dentinal tubules, and can accelerate remineralization. However, mere use of calcium phosphate particles as small as 900 nm or less allows dissolution of the particles having a large specific surface area rather than calcification in oral environments, and it is problematic in that initial physical sealing is not achieved certainly and the sealing is removed by a physical stimulus such as gargling, or eating and drinking.

Patent Document 3 discloses a two-component type dentinal tubule sealant obtained by mixing a material formed of tetracalcium phosphate particles and an alkali metal salt of phosphoric acid with a material containing water to convert them into hydroxyapatite. This sealant allows hydroxyapatite to deposit even at deep parts of dentinal tubules and can seal dentinal tubules densely, but there remains room for reducing the labor in extemporaneous preparation by an operator or improving storage stability when forming a one-component type agent.

Patent Document 4 discloses a two-component dentinal tubule sealant obtained by mixing a material formed of poorly-soluble calcium phosphate particles and a phosphorus-free calcium compound with a material containing water, thereby converting them into hydroxyapatite gradually. This sealant excels in dentinal tubule sealability immediately after treatment and also excels in the durability of dentinal tubule sealing, but there remains room for reducing the labor in extemporaneous preparation by an operator or improving storage stability when forming a one-component type agent.

As disclosed in the above-cited patent documents, the disclosed products are insufficient in initial dentinal tubule sealability or are problematic in the durability of dentinal tubule sealing or require extemporaneous preparation or have room for improving storage stability when forming a one-component type agent.

PRIOR ART DOCUMENTS

Patent Documents

Patent Document 1: JP 10-17449 A
Patent Document 2: JP 2005-325102 A
Patent Document 3: WO 2010/113800 A1
Patent Document 4: WO 2012/046667 A1

SUMMARY OF THE INVENTION

Problems to be Solved by the Invention

The present invention was devised in order to solve the above-mentioned problems and aims to provide a dentinal tubule sealant excelling in dentinal tubule sealability immediately after treatment, durability of dentinal tubule sealing, ease of operation, and storage stability.

Means for Solving the Problems

The above-mentioned problems can be solved by providing a dentinal tubule sealant containing apatite particles (A) having an average particle diameter of 500 nm or less, a filler (B) having an average particle diameter of 1 to 10 µm, and a dispersant (C), wherein the weight ratio (A/B) of the apatite particles (A) to the filler (B) is 0.05 to 15, the dentinal tubule sealant contains 15 to 95 parts by weight of the dispersant (C) relative to 100 parts by weight in total of the apatite particles (A) and the filler (B), and the total amount of the apatite particles (A), the filler (B), and the dispersant (C) is 85 parts by weight or more relative to 100 parts by weight of the dentinal tubule sealant.

It is preferable here that the filler (B) is an inorganic filler (b) and/or an organic filler (b'). It is preferable that the filler (B) is at least one inorganic filler (b) selected from the group consisting of basic calcium phosphate particles (b1), poorly-soluble calcium phosphate particles (b2), a phosphorus-free calcium compound (b3), and an inorganic filler (b4) other than (b1) to (b3).

It is preferable that the filler (B) is an inorganic filler (b) selected from a mixture of basic calcium phosphate particles (b1) and poorly-soluble calcium phosphate particles (b2) and a mixture of poorly-soluble calcium phosphate particles (b2) and a phosphorus-free calcium compound (b3), and the Ca/P ratio of the sum of (b1) and (b2) or the sum of (b2) and (b3) is 1.2 to 2.0.

It is preferable here that the filler (B) is an inorganic filler (b) containing a mixture of basic calcium phosphate particles (b1), poorly-soluble calcium phosphate particles (b2) and a phosphorus-free calcium compound (b3), and the Ca/P ratio of the sum of (b1), (b2) and (b3) is 1.5 to 3.0.

It is preferable that the inorganic filler (b) further contains an inorganic filler (b4) other than (b1) to (b3), and it is preferable that the dispersant (C) is water and/or a nonaqueous liquid. It is preferable that the nonaqueous liquid is at least one selected from the group consisting of a polyether, a monohydric alcohol, and a polyhydric alcohol.

Effects of the Invention

A dentinal tubule sealant excelling in dentinal tubule sealability immediately after treatment, durability of dentinal tubule sealing, ease of operation, and storage stability is provided by the present invention. In particular, because of its excellent storage stability, it is not necessary to prepare the dentinal tubule sealant at a medical site and the dentinal tubule sealant can be used as a one-component type dentinal tubule sealant.

MODE FOR CARRYING OUT THE INVENTION

The dentinal tubule sealant of the present invention contains apatite particles (A) having an average particle diameter of 500 nm or less, a filler (B) having an average particle diameter of 1 to 10 μm, and a dispersant (C). It was revealed by the present inventors that the dentinal tubule sealability immediately after treatment and the effect thereof are sustained by incorporating the apatite particles (A) having an average particle diameter of 500 nm or less and the filler (B) having an average particle diameter of 1 to 10 μm in a certain ratio into the dispersant (C). Although the mechanism of action of this effect is not necessarily clear, the following mechanism is conceivable.

The filler (B) having an average particle diameter of 1 to 10 μm used in the present invention is believed to be able to enter physically into dentinal tubules being several micrometers in depth from the surface layer immediately after treatment, and able to fill up most of the tubule volume. Further adding of the apatite particles (A) having an average particle diameter of 500 nm or less to this system and allowing them to exist therein enables efficient filling of gaps between particles and, as a result, it seems that dentinal tubules immediately after treatment can be sealed surely with a dense sealing material. The apatite particles (A) having an average particle diameter of 500 nm or less seem to serve as nuclei to undergo crystal growth and accelerate calcification of the inside of tubules on coming into contact with a tubule inner fluid or saliva containing calcium ions or phosphate ions supersaturated relative to hydroxyapatite, which is the primary constituent of tooth substance. Moreover, the crystal-grown calcified substance seems to calcify also dentinal tubule walls and surrounding dentin to unify them with dentin eventually, and the resulting tubule sealing material seems not to be decayed or removed even in the presence of "pulpal pressure", which is pressure with which the pulpal fluid flows out from the dental pulp toward a surface of the tooth substance, as well as seems to more calcify a sealing material utilizing the pulpal fluid. The adoption of the configuration of the present invention is significant in that tubules in a dentin surface layer are sealed efficiently with the filler (B) having an average particle diameter of 1 to 10 μm, which has an average particle diameter the same as or larger than dentinal tubules being 1 to 2 μm in diameter, and it fills up gaps between such particles and the filler itself undergoes crystal growth and accelerates calcification due to its environment.

For the dentinal tubule sealant of the present invention, apatite particles (A) having an average particle diameter of 500 nm or less are used. When the average particle diameter of the apatite particles (A) is greater than 500 nm, they cannot efficiently fill gaps between particles of the filler (B) having an average particle diameter of 1 to 10 μm in dentinal tubules, and moreover they may hardly serve as nuclei of crystal growth due to their increased specific surface area. The average particle diameter of the apatite particles (A) is more preferably 300 nm or less, particularly preferably 200 nm or less. On the other hand, the average particle diameter of the apatite particles (A) is preferably 10 nm or more. When the average particle diameter of the apatite particles (A) is less than 10 nm, there is a possibility that the resulting dentinal tubule sealant increases in viscosity remarkably and thus possesses tacky paste properties and decreases in operability. The average particle diameter of the apatite particles (A) is more preferably 20 nm or more, even more preferably 30 nm or more. The average particle diameter of the apatite particles (A) as used herein is one determined via measurement by electron microscopic observation and calculation.

In the electron microscopic observation, the average particle diameter can be determined, for example, by taking a photograph of the particles by a transmission electron microscope (H-800NA, manufactured by Hitachi, Ltd.) and measuring the particle diameter of particles (100 or more particles) observed in a unit field of view of the photograph by image analyzing particle size distribution analysis software (Macview (Mountech Co., Ltd.)). The particle diameter of a particle is determined as an equivalent circular diameter, which is the diameter of a circle having the same area as the particle, and an average primary particle diameter is calculated from the number of particles and their particle diameters.

The apatite particles (A) having an average particle diameter of 500 nm or less used in the present invention are not particularly limited, but they are preferably one or more selected from the group consisting of hydroxyapatite $[Ca_{10}(PO_4)_6(OH)_2]$, carbonate apatite $[Ca_{10}(PO_4)_6CO_3]$, fluoroapatite $[Ca_{10}(PO_4)_6F_2]$, and chlorapatite $[Ca_{10}(PO_4)_6Cl_2]$. Of these, at least one selected from the group consisting of hydroxyapatite $[Ca_{10}(PO_4)_6(OH)_2]$, carbonate apatite $[Ca_{10}(PO_4)_6CO_3]$, and fluoroapatite $[Ca_{10}(PO_4)_6F_2]$ is used more preferably, and especially, hydroxyapatite $[Ca_{10}(PO_4)_6$ $(OH)_2$] is used even more preferably from the viewpoints of being a primary constituent of tooth substance and of crystal growth of hydroxyapatite in dentinal tubules.

The method for the production of the apatite particles (A) used in the present invention is not particularly limited, and a marketed product may be used if available, and the marketed product may be pulverized. In this case, a pulverizing apparatus such as a ball mill, a pestle and mortar machine, and a jet mill can be used. The apatite particles (A) can be obtained also by pulverizing the apatite particles (A) together with a liquid medium such as an alcohol by using a pestle and mortar machine, a ball mill, or the like, thereby preparing a slurry, and then drying the resulting slurry. It is preferable to use a ball mill as the pulverizing apparatus for this purpose, and as the material of its pot and balls, alumina or zirconia is preferably adopted.

For the dentinal tubule sealant of the present invention, a filler (B) having an average particle diameter of 1 to 10 μm is used. When the average particle diameter of the filler (B) is less than 1 μm, there is a possibility that the filler cannot seal dentinal tubules efficiently, and there is also a possibility that the dentinal tubule sealing ratio immediately after treatment lowers; thus, the average particle diameter of the filler (B) is preferably 1.5 μm or more. On the other hand, when the average particle diameter of the filler (B) is larger than 10 μm, there is a possibility that particles thereof cannot enter dentinal tubules; thus, the average particle diameter of the filler (B) is more preferably 8 μm or less, particularly preferably 6 μm or less. The average particle diameter of the filler (B) used in the present invention is one determined via measurement by a laser diffraction/scattering method using a laser diffraction particle size distribution analyzer and calculation.

Regarding the laser diffraction/scattering method, measurement can be performed, for example, by means of a laser diffraction particle size distribution analyzer (SALD-2100, manufactured by Shimadzu Corporation) using a 0.2% aqueous solution of sodium hexametaphosphate as a dispersion medium.

The filler (B) having an average particle diameter of 1 to 10 μm used in the present invention, which is not particularly limited, is preferably an inorganic filler (b) and/or an organic filler (b'). Especially, it is more preferable from the viewpoint of the durability of dentinal tubule sealing that the filler (B) is composed of only the inorganic filler (b). As the inorganic filler (b), at least one inorganic filler (b) selected from the group consisting of basic calcium phosphate particles (b1), poorly-soluble calcium phosphate particles (b2), a phosphorus-free calcium compound (b3), and an inorganic filler (b4) other than (b1) to (b3) is preferable from the viewpoint of the durability of dentinal tubule sealing. Especially, as the inorganic filler (b), at least one selected from the group consisting of a mixture of basic calcium phosphate particles (b1) and poorly-soluble calcium phosphate particles (b2), a mixture of poorly-soluble calcium phosphate particles (b2) and a phosphorus-free calcium compound (b3), a mixture of basic calcium phosphate particles (b1), poorly-soluble calcium phosphate particles (b2) and a phosphorus-free calcium compound (b3), a mixture of basic calcium phosphate particles (b1), poorly-soluble calcium phosphate particles (b2) and an inorganic filler (b4) other than (b1) to (b3), and a mixture of poorly-soluble calcium phosphate particles (b2), a phosphorus-free calcium compound (b3) and an inorganic filler (b4) other than (b1) to (b3) is more preferable. From the viewpoint of the dentinal tubule sealability immediately after treatment and the durability of dentinal tubule sealing, the inorganic filler (b) is most preferably a mixture of basic calcium phosphate particles (b1), poorly-soluble calcium phosphate particles (b2) and a phosphorus-free calcium compound (b3).

The organic filler (b') used in the present invention is preferably composed of one or more selected from the group consisting of polycarbonate, polyepoxide, melamine resin, polymethyl methacrylate, polyethyl methacrylate, methyl methacrylate-ethyl methacrylate copolymer, crosslinked polymethyl methacrylate, crosslinked polyethyl methacrylate, polyamide, polyvinyl chloride, polystyrene, chloroprene rubber, nitrile rubber, an ethylene-vinyl acetate copolymer, a styrene-butadiene copolymer, an acrylonitrile-styrene copolymer, and an acrylonitrile-styrene-butadiene copolymer.

The method for the production of the organic filler (b') used in the present invention is not particularly limited, and a marketed product may be used if available, and the marketed product may be pulverized. In this case, a pulverizing apparatus such as a ball mill, a pestle and mortar machine, and a jet mill can be used.

The basic calcium phosphate particles (b1) used in the present invention, which are not particularly limited, are preferably at least one species selected from the group consisting of tetracalcium phosphate [$Ca_4(PO_4)_2O$] particles, octacalcium phosphate pentahydrate [$Ca_8H_2(PO_4)_6 \cdot 5H_2O$] particles, and apatite particles. Among these, at least one selected from the group consisting of tetracalcium phosphate [$Ca_4(PO_4)_2O$] particles and apatite particles is more preferable from the viewpoint of the dentinal tubule sealability immediately after treatment and durability of dentinal tubule sealing. Tetracalcium phosphate [$Ca_4(PO_4)_2O$] particles are used even more preferably.

The poorly-soluble calcium phosphate particles (b2) used in the present invention, which are not particularly limited, are preferably at least one selected from the group consisting of anhydrous calcium monohydrogen phosphate [$CaHPO_4$] particles (hereinafter sometimes abbreviated to DCPA), tricalcium phosphate [$Ca_3(PO_4)_2$] particles, anhydrous calcium dihydrogen phosphate [$Ca(H_2PO_4)_2$] particles, amorphous calcium phosphate [$Ca_3(PO_4) \cdot xH_2O$] particles, calcium dihydrogen pyrophosphate [$CaH_2P_2O_7$] particles, calcium monohydrogen phosphate dihydrate [$CaHPO_4 \cdot 2H_2O$] particles, and calcium dihydrogen phosphate monohydrate [$Ca(H_2PO_4)_2 \cdot H_2O$] particles. Among these, at least one selected from the group consisting of anhydrous calcium monohydrogen phosphate [$CaHPO_4$] particles, tricalcium phosphate [$Ca_3(PO_4)_2$] particles, and anhydrous calcium dihydrogen phosphate [$Ca(H_2PO_4)_2$] particles is used more preferably used. Especially, from the viewpoints of the dentinal tubule sealability immediately after treatment and durability of dentinal tubule sealing, at least one selected from the group consisting of anhydrous calcium monohydrogen phosphate [$CaHPO_4$] particles and tricalcium phosphate [$Ca_3(PO_4)_2$] is used preferably. Among tricalcium phosphate [$Ca_3(PO_4)_2$] particles, α-tricalcium phosphate [α-$Ca_3(PO_4)_2$] particles (hereinafter sometimes abbreviated to α-TCP) are used preferably.

While the phosphorus-free calcium compound (b3) used in the present invention is not particularly limited, examples thereof include calcium hydroxide [$Ca(OH)_2$], calcium oxide [$CaO$], calcium chloride [$CaCl_2$], calcium nitrate [$Ca(NO_3)_2 \cdot nH_2O$], calcium acetate [$Ca(CH_3CO_2)_2 \cdot nH_2O$], calcium lactate [$C_6H_{10}CaO_6$], calcium citrate [$Ca_3(C_6H_5O_7)_2 \cdot nH_2O$], calcium metasilicate [$CaSiO_3$], dicalcium silicate [$Ca_2SiO_4$], tricalcium silicate [$Ca_3SiO_5$], and calcium carbonate [$CaCO_3$], and one or more of these are used preferably. From the viewpoint of the dentinal tubule sealability immediately after treatment and durability of dentinal tubule sealing, at least one selected from the group consisting of calcium hydroxide, calcium carbonate, calcium metasilicate, dicalcium silicate, and tricalcium silicate is more preferable, and at least one selected from the group consisting of calcium hydroxide and calcium carbonate is used more preferably.

The inorganic filler (b4) other than (b1) to (b3) used in the present invention is an inorganic filler other than the abovementioned (b1), (b2) and (b3). While the inorganic filler (b4) other than (b1) to (b3) used in the present invention is not particularly limited, examples thereof include quartz, silica, alumina, zirconia, titania, silica-titania, silica-titania-barium oxide, silica-zirconia, silica-alumina, lanthanum glass, borosilicate glass, soda glass, barium glass, strontium glass, glass ceramics, aluminosilicate glass, barium boroaluminosilicate glass, strontium boroaluminosilicate glass, fluoroaluminosilicate glass, calcium fluoroaluminosilicate glass, strontium fluoroaluminosilicate glass, barium fluoroaluminosilicate glass, and strontium calcium fluoroaluminosilicate glass, and one or more of these are used preferably. Among these, at least one selected from the group consisting of barium glass, fluoroaluminosilicate glass, silica, and zirconia is used more preferably.

In the present invention, the method for the production of the basic calcium phosphate particles (b1), the poorly-soluble calcium phosphate particles (b2), the phosphorus-free calcium compound (b3), and the inorganic filler (b4) other than (b1) to (b3) used as the inorganic filler (b) is not particularly limited, and a marketed product may be used if available, and the marketed product may be further pulverized. In this case, a pulverizing apparatus such as a ball mill, a pestle and mortar machine, and a jet mill can be used. The inorganic filler (b) can be obtained also by pulverizing the inorganic filler (b) together with a liquid medium such as an alcohol by using a pestle and mortar machine, a ball mill, or the like, thereby preparing a slurry, and then drying the resulting slurry. It is preferable to use a ball mill as the pulverizing apparatus for this purpose, and as the material of its pot and balls, alumina or zirconia is preferably adopted.

In the present invention, when the inorganic filler (B) is an inorganic filler (b) selected from a mixture of basic calcium phosphate particles (b1) and poorly-soluble calcium phosphate particles (b2) and a mixture of poorly-soluble calcium phosphate particles (b2) and a phosphorus-free calcium compound (b3), it is preferable that the Ca/P ratio of the sum of (b1) and (b2) or the sum of (b2) and (b3) is 1.2 to 2.0, more preferably 1.3 to 1.8, particularly preferably 1.5 to 1.7. When the inorganic filler (B) is an inorganic filler (b) containing a mixture of basic calcium phosphate particles (b1), poorly-soluble calcium phosphate particles (b2) and a phosphorus-free calcium compound (b3), it is preferable that the Ca/P ratio of the sum of (b1), (b2) and (b3) is 1.5 to 3.0, more preferably 1.6 to 2.9, particularly preferably 1.7 to 2.8. This can afford a one-component type dentinal tubule sealant of the present invention, which excels in dentinal tubule sealability immediately after treatment and the durability of dentinal tubule sealing. It is a preferable embodiment of the present invention that an inorganic filler (b4) other than (b1) to (b3) is further contained in the inorganic filler (b).

The dispersant (C) used in the present invention, which is not particularly limited, is preferably water and/or a nonaqueous liquid. Examples of the nonaqueous liquid include polyethers, such as polyethylene glycol and polypropylene glycol, monohydric alcohols, such as ethanol and methanol, and polyhydric alcohols, such as glycerol, ethylene glycol, propylene glycol, and diglycerol, and it is preferable that the nonaqueous liquid is at least one nonaqueous liquid selected from the group consisting of a polyether, a monohydric alcohol, and a polyhydric alcohol. Especially from the viewpoint of operativity, it is more preferable that the nonaqueous liquid is at least one selected from the group consisting of water, a polyether, and a polyhydric alcohol, it is further preferable that the nonaqueous liquid is at least one selected from the group consisting of water, glycerol, and polyethylene glycol, and it is most preferable that the nonaqueous liquid is glycerol and/or polyethylene glycol.

The dentinal tubule sealant of the present invention contains 15 to 95 parts by weight of the dispersant (C) relative to 100 parts by weight in total of the apatite particles (A) and the filler (B). When the amount of the dispersant (C) is less than 15 parts by weight, there is a possibility that a paste cannot be formed. Thus, the amount is preferably 20 parts by weight or more, more preferably 25 parts by weight or more. On the other hand, when the amount of the dispersant (C) exceeds 95 parts by weight, there is a possibility that dentinal tubules cannot be sealed sufficiently. Thus, the amount is preferably 90 parts by weight or less, more preferably 85 parts by weight or less.

In the dentinal tubule sealant of the present invention, the weight ratio (A/B) of the apatite particles (A) to the filler (B) is 0.05 to 15. When the weight ratio (A/B) is less than 0.05, the apatite particles (A) in an amount large enough for fully filling gaps between particles of the filler (B) filled into dentinal tubules cannot be secured and the initial dentinal tubule sealability may be poor. Moreover, it is not possible to secure the apatite particles (A) in an amount large enough for enabling hydroxyapatite to undergo crystal growth in dentinal tubules and the durability of dentinal tubule sealing may deteriorate. The weight ratio (A/B) is preferably 0.3 or more, particularly preferably 0.5 or more. On the other hand, when the weight ratio (A/B) exceeds 15, the filler (B) is not filled into dentinal tubules efficiently immediately after treatment and the dentinal tubule sealability immediately after treatment may deteriorate. Moreover, the number of apatite particles (A) having a large specific surface area increases, so that dissolution of a sealing material itself readily proceeds and the initial dentinal tubule sealability may deteriorate, or alternatively the durability of dentinal tubule sealing may deteriorate, for example, a sealing material may be removed after treatment by a physical stimulus such as gargling, or eating and drinking. The weight ratio (A/B) is more preferably 3 or less, particularly preferably 2 or less.

In the dentinal tubule sealant of the present invention, the total amount of the apatite particles (A), the filler (B), and the dispersant (C) is 85 parts by weight or more relative to 100 parts by weight of the dentinal tubule sealant. When the total amount of the apatite particles (A), the filler (B), and the dispersant (C) is less than 85 parts by weight, the dentinal tubule sealant may not be able to seal dentinal tubules sufficiently. Thus, the amount is preferably 90 parts by weight or more, more preferably 95 parts by weight or more.

The dentinal tubule sealant of the present invention may also contain a fluorine compound as necessary. This makes it possible to enhance the acid resistance of a sealing material. The fluorine compound used in the present invention is not particularly limited, and examples thereof include one or more species selected from sodium fluoride, potassium fluoride, ammonium fluoride, lithium fluoride, cesium fluoride, magnesium fluoride, calcium fluoride, strontium fluoride, strontium fluoride, barium fluoride, copper fluoride, zirconium fluoride, aluminum fluoride, stannous fluoride, sodium monofluorophosphate, potassium monofluorophosphorate, hydrofluoric acid, titanium sodium fluoride, titanium potassium fluoride, hexylamine hydrofluoride, laurylamine hydrofluoride, glycine hydrofluoride, alanine hydrofluoride, fluorosilanes, and diamine silver fluoride. Among these, sodium fluoride, sodium monofluorophosphate, and stannous fluoride are preferably used from the viewpoint of safety.

The amount of the fluorine compound used in the present invention is not particularly limited, and it is preferable that 0.01 to 10 parts by weight of the fluorine compound in terms of fluoride ion is contained relative to 100 parts by weight in total of the dentinal tubule sealant. When the amount of the fluorine compound in terms of fluoride ion is less than 0.01 parts by weight, there is a possibility that the acid resistance of a sealing material is low. Thus, the amount is more preferably 0.05 parts by weight or more. On the other hand, when the amount of the fluorine compound in terms of fluoride ion exceeds 10 parts by weight, there is a possibility that the safety is deteriorated. Thus, the amount is more preferably 5 parts by weight or less.

The dentinal tubule sealant of the present invention may also contain a thickener as necessary. This is because the viscosity of a paste can be adjusted and the paste can be adjusted to have properties easy to be handled by operators. Examples of the thickener include one or more species selected from fumed silica, carboxymethylcellulose, sodium carboxymethylcellulose, hydroxypropylcellulose, hydroxypropylmethylcellulose, polyvinyl alcohol, polyacrylic acid, polystyrene sulfonic acid, polystyrene sulfonic acid salts, polyglutamic acid, polyglutamic acid salts, polyaspartic acid, polyaspartic acid salts, poly-L-lysine, poly-L-lysine salts, starch other than cellulose, alginic acid, alginic acid salts, carrageenan, guar gum, xanthan gum, cellulose gum, hyaluronic acid, hyaluronic acid salts, polysaccharides such as pectin, pectin salts, chitin and chitosan, acidic polysaccharide esters such as propylene glycol alginate, and polymers such as proteins, e.g. collagen, gelatin and derivatives thereof. In particular, fumed silica is preferably used because the use thereof readily leads to desired paste properties.

The amount of the thickener used in the present invention is not particularly limited, and 0.01 to 10 parts by weight of the thickener is preferably contained relative to 100 parts by weight in total of the dentinal tubule sealant. When the amount of the thickener is less than 0.01 parts by weight, there is a possibility that the paste increases excessively in flowability and becomes difficult to operate, and thus the amount is more preferably 0.05 parts by weight or more. On the other hand, when the amount of the thickener exceeds 10 parts by weight, there is a possibility that the paste decreases excessively in flowability and becomes difficult to operate, and thus the amount is more preferably 8 parts by weight or less.

The dentinal tubule sealant of the present invention can contain any pharmacologically acceptable drugs or the like as necessary. Examples of such drugs include antibacterial agents typified by cetyl pyridinium chloride, sodium benzoate, methyl paraben, esters of p-hydroxybenzoic acid, and alkyl diaminoethylglicyne hydrochloric acid, disinfectants, anticancer drugs, antibiotics, blood circulation improvers such as Actosin and PEG1, growth factors such as bFGF, PDGF and BMP, osteoblasts, odontoblasts, and undifferentiated bone marrow-derived stem cells, embryonic stem (ES) cells, induced pluripotent stem (iPS) cells produced by dedifferentiating differentiated cells such as fibroblasts by gene introduction, and cells which promote hard tissue formation, such as cells produced by differentiating the foregoing. These drugs can be blended in the dentinal tubule sealant of the present invention.

The dentinal tubule sealant of the present invention can contain a sweetener as necessary. Examples of such a sweetener include one or more selected from sugar alcohols, such as saccharin sodium, xylitol, stevioside, xylitol, sorbitol, and erythritol, and artificial sweeteners, such as aspartame, acesulfame potassium, glycyrrhiza extract, saccharin, and saccharin sodium.

The dentinal tubule sealant of the present invention can contain a flavor as necessary. Examples of such a flavor include one or more selected from menthol, orange oil, spearmint oil, peppermint oil, lemon oil, eucalyptus oil, methyl salicylate, etc.

The dentinal tubule sealant of the present invention excels in dentinal tubule sealability immediately after treatment, durability of dentinal tubule sealing, ease of operation, and storage stability. In particular, because of its excellent storage stability, it is not necessary to prepare the dentinal tubule sealant at a medical site and the dentinal tubule sealant can be used as a one-component type dentinal tubule sealant.

EXAMPLES

The present invention is described concretely below with reference to examples. With regard to the average particle diameter of the apatite particles and the filler (B) in the examples, measurement was conducted using a laser diffraction particle size distribution analyzer ("SALD-2100" manufactured by Shimadzu Corporation), and a median diameter calculated from the result of the measurement was defined as the average particle diameter.

[Preparation of Apatite Particles]
(a) Hydroxyapatite Particles (A) Having an Average Particle Diameter of 40 nm Commercially available hydroxyapatite particles (SHAp manufactured by SofSera Corporation, spherical) were used as received as hydroxyapatite particles having an average particle diameter of 40 nm.

(b) Hydroxyapatite Particles (A) Having an Average Particle Diameter of 150 nm

Commercially available hydroxyapatite particles (SHAp manufactured by SofSera Corporation, rod-shaped) were used as received as hydroxyapatite particles having an average particle diameter of 150 nm.

(c) Hydroxyapatite Particles (A) Having an Average Particle Diameter of 400 nm

Hydroxyapatite particles having an average particle diameter of 400 nm were obtained by single treatment of commercially available hydroxyapatite particles (HAP-200 manufactured by Taihei Chemical Industrial Co., Ltd., having an average particle diameter of 5 to 20 μm) with a Nanojetmizer (Model NJ-100 manufactured by Aishin Nano Technologies CO., LTD.) with the grinding pressure condition adjusted to feeding pressure of 0.7 MPa and grinding pressure of 0.7 MPa, and the treated amount condition adjusted to 8 kg/hr.

[Preparation of Filler (B)]
(1) Preparation of Basic Calcium Phosphate Particles (b1)
(a) Tetracalcium Phosphate (TTCP) Particles Having an Average Particle Diameter of 2 μm Tetracalcium phosphate (TTCP) particles having an average particle diameter of 2 μm were obtained by single treatment of commercially available Tetracalcium phosphate particles (TTCP manufactured by Taihei Chemical Industrial Co., Ltd.) with a Nanojetmizer (Model NJ-100 manufactured by Aishin Nano Technologies CO., LTD.) with the grinding pressure condition adjusted to feeding pressure of 0.7 MPa and grinding pressure of 0.7 MPa, and the treated amount condition adjusted to 8 kg/hr.

(b) Hydroxyapatite Particles Having an Average Particle Diameter of 2 μm

Hydroxyapatite particles having an average particle diameter of 2 μm were obtained by single treatment of commercially available hydroxyapatite particles (HAP-200 manufactured by Taihei Chemical Industrial Co., Ltd., having an average particle diameter of 5 to 20 μm) with a Nanojetmizer (Model NJ-100 manufactured by Aishin Nano Technologies CO., LTD.) with the grinding pressure condition adjusted to feeding pressure of 0.7 MPa and grinding pressure of 0.7 MPa, and the treated amount condition adjusted to 8 kg/hr.

(c) Hydroxyapatite Particles Having an Average Particle Diameter of 10 μm

Commercially available hydroxyapatite particles (HAP-200 manufactured by Taihei Chemical Industrial Co., Ltd., having an average particle diameter of 5 to 20 μm) were used as received as hydroxyapatite particles having an average particle diameter of 10 μm.

(2) Preparation of Poorly-Soluble Calcium Phosphate Particles (b2)

The anhydrous calcium monohydrogen phosphate (DCPA) particles (b2) used in the examples were obtained by pulverizing commercially available anhydrous calcium monohydrogen phosphate particles (The Japanese Pharmacopoeia, manufactured by Taihei Chemical Industrial Co., Ltd., having an average particle diameter of 20 μm) by the methods described below.

(a) Anhydrous Calcium Monohydrogen Phosphate Particles (b2) Having an Average Particle Diameter of 1 μm Anhydrous calcium monohydrogen phosphate particles (b2) having an average particle diameter of 1 μm were obtained as follows. 50 g of commercially available anhydrous calcium monohydrogen phosphate particles (The Japanese Pharmacopoeia, manufactured by Taihei Chemical Industrial Co., Ltd., having an average particle diameter of 20 μm), 120 g of 95% ethanol ("Ethanol (95)" manufactured by Wako Pure Chemical Industries, Ltd.), and 240 g of zirconia balls being 10 mm in diameter were put into a 400-ml grinding pot made of alumina ("Type A-3 HD Pot Mill" manufactured by Nikkato Corporation) and subsequently wet pulverized at a rotation speed of 120 rpm for 48 hours to obtain a slurry. Then, the slurry was distilled with a rotary evaporator to remove ethanol, followed by drying at 60° C. for 6 hours and further vacuum drying at 60° C. for 24 hours.

(b) Anhydrous Calcium Monohydrogen Phosphate Particles (b2) Having an Average Particle Diameter of 2 μm Anhydrous calcium monohydrogen phosphate particles (b2) having an average particle diameter of 2 μm were obtained as follows. 50 g of commercially available anhydrous calcium monohydrogen phosphate particles (The Japanese Pharmacopoeia, manufactured by Taihei Chemical Industrial Co., Ltd., having an average particle diameter of 20 μm), 120 g of 95% ethanol ("Ethanol (95)" manufactured by Wako Pure Chemical Industries, Ltd.), and 240 g of zirconia balls being 10 mm in diameter were put into a 400-ml grinding pot made of alumina ("Type A-3 HD Pot Mill" manufactured by Nikkato Corporation) and subsequently wet pulverized at a rotation speed of 120 rpm for 36 hours to obtain a slurry. Then, the slurry was distilled with a rotary evaporator to remove ethanol, followed by drying at 60° C. for 6 hours and further vacuum drying at 60° C. for 12 hours.

(c) Anhydrous Calcium Monohydrogen Phosphate Particles (b2) Having an Average Particle Diameter of 8 μm Anhydrous calcium monohydrogen phosphate particles (b2) having an average particle diameter of 8 μm were obtained as follows. 50 g of commercially available anhydrous calcium monohydrogen phosphate particles (The Japanese Pharmacopoeia, manufactured by Taihei Chemical Industrial Co., Ltd., having an average particle diameter of 20 μm), 120 g of 95% ethanol ("Ethanol (95)" manufactured by Wako Pure Chemical Industries, Ltd.), and 240 g of zirconia balls being 10 mm in diameter were put into a 400-ml grinding pot made of alumina ("Type A-3 HD Pot Mill" manufactured by Nikkato Corporation) and subsequently wet pulverized at a rotation speed of 120 rpm for 20 hours to obtain a slurry. Then, the slurry was distilled with a rotary evaporator to remove ethanol, followed by drying at 60° C. for 6 hours and further vacuum drying at 60° C. for 12 hours.

(d) Anhydrous Calcium Monohydrogen Phosphate Particles Having an Average Particle Diameter of 20 μm Commercially available anhydrous calcium monohydrogen phosphate particles (The Japanese Pharmacopoeia, manufactured by Taihei Chemical Industrial Co., Ltd., having an average particle diameter of 20 μm) were used as received as anhydrous calcium monohydrogen phosphate particles having an average particle diameter of 20 μm.

(e) Anhydrous Calcium Monohydrogen Phosphate Particles Having an Average Particle Diameter of 0.5

Anhydrous calcium monohydrogen phosphate particles having an average particle diameter of 0.5 μm were obtained as follows. 50 g of commercially available anhydrous calcium monohydrogen phosphate particles (The Japanese Pharmacopoeia, manufactured by Taihei Chemical Industrial Co., Ltd., having an average particle diameter of 20 μm), 120 g of 95% ethanol ("Ethanol (95)" manufactured by Wako Pure Chemical Industries, Ltd.), and 240 g of zirconia balls being 10 mm in diameter were put into a 400-ml grinding pot made of alumina ("Type A-3 HD Pot Mill" manufactured by Nikkato Corporation) and subsequently wet pulverized at a rotation speed of 120 rpm for 48 hours to obtain a slurry. Then, the slurry was distilled with a rotary evaporator to remove ethanol, followed by drying at 60° C. for 6 hours and further vacuum drying at 60° C. for 12 hours.

(f) Tricalcium Phosphate Particles (b2) Having an Average Particle Diameter of 2 μm Commercially available α-tricalcium phosphate (manufactured by Taihei Chemical Industrial Co., Ltd.) was used as received as tricalcium phosphate (α-TCP) particles (b2) having an average particle diameter of 2 μm.

(3) Preparation of Phosphorus-Free Calcium Compound (b3)

(a) Calcium Carbonate Particles (b3) Having an Average Particle Diameter of 2 μm Commercially available calcium carbonate (precipitated calcium carbonate, manufactured by Yabashi Industries Co., Ltd.) was used as received as calcium carbonate particles (b3) having an average particle diameter of 2 μm.

(b) Calcium Hydroxide Particles (b3) Having an Average Particle Diameter of 2 μm Calcium hydroxide particles (b3) having an average particle diameter of 2 μm were obtained as follows. 50 g of commercially available calcium hydroxide particles (manufactured by KAWAI LIME INDUSTRY Co., Ltd., having an average particle diameter of 14.5 μm), 240 g of 99.5% ethanol ("Ethanol, Dehydrated (99.5)" manufactured by Wako Pure Chemical Industries, Ltd.) and 480 g of zirconia balls having a diameter of 10 mm were put into a 1000-ml grinding pot made of alumina ("HD-B-104 Pot Mill" manufactured by Nikkato Corporation) and subsequently subjected to wet vibration pulverization at a rotation speed of 1500 rpm for 7 hours to obtain a slurry. Then, the slurry was distilled with a rotary evaporator to remove ethanol, followed by drying at 60° C. for 6 hours.

(c) Calcium Silicate Particles (b3) Having an Average Particle Diameter of 2 μm

Calcium silicate particles (b3) having an average particle diameter of 2 μm were obtained as follows. 50 g of commercially available calcium silicate particles (manufactured by Wako Pure Chemical Industries, Ltd.), 240 g of 99.5% ethanol ("Ethanol, Dehydrated (99.5)" manufactured by Wako Pure Chemical Industries, Ltd.) and 480 g of zirconia balls having a diameter of 10 mm were put into a 1000-ml grinding pot made of alumina ("HD-B-104 Pot Mill" manufactured by Nikkato Corporation) and subsequently subjected to wet vibration pulverization at a rotation speed of 1500 rpm for 24 hours to obtain a slurry. Then, the slurry was distilled with a rotary evaporator to remove ethanol, followed by drying at 60° C. for 6 hours.

(d) Calcium Carbonate Particles (b3) Having an Average Particle Diameter of 2.6 μm A product manufactured by Yabashi Industries Co., Ltd. was used as received as calcium carbonate particles (b3) having an average particle diameter of 2.6 μm.

(4) Preparation of Inorganic Filler (b4) Other than (b1) to (b3)

(a) Ba Glass Particles (b4) Having an Average Particle Diameter of 2 μm

Commercially available Ba glass particles (G018-186, manufactured by SCHOTT) were used as received as Ba glass particles (b4) having an average particle diameter of 2 μm.

(b) Fluoroaluminosilicate Glass Particles (b4) Having an Average Particle Diameter of 2 μm Commercially available fluoroaluminosilicate glass particles (G018-117, manufactured by SCHOTT) were used as received as fluoroaluminosilicate (FAS) glass particles (b4) having an average particle diameter of 2 μm.

(c) Zirconia Particles (b4) Having an Average Particle Diameter of 2 μm

Commercially available zirconia particles (manufactured by Soekawa Chemical Co., Ltd.) were used as received as zirconia particles (b4) having an average particle diameter of 2 μm.

(5) Preparation of Organic Filler (b')

A commercially available melamine resin (EPOSTAR, manufactured by NIPPON SHOKUBAI CO., LTD.) was used as received as melamine resin particles (b') having an average particle diameter of 2 μm.

[Preparation of Dispersant (C)]

Two types of polyethylene glycol differing in molecular weight (MACROGOL 400, MACROGOL 4000, manufactured by Sanyo Chemical Industries, Ltd.), glycerol (manufactured by Wako Pure Chemical Industries, Ltd.), and water (purified water conforming to The Japanese Pharmacopoeia, manufactured by Takasugi Pharmaceutical Co., Ltd.), all commercially available, were used as received.

[Preparation of Fluorine Compound and Thickener]

Commercially available sodium fluoride (manufactured by Wako Pure Chemical Industries, Ltd.) was used as received as sodium fluoride (NaF), a fluorine compound, and two types of commercially available fumed silica (Ar-130, Ar-380, manufactured by Nippon Aerosil Co., Ltd.), thickeners, were used as received.

[Preparation of Dentinal Tubule Sealant]

Examples 1 to 103, Comparative Examples 1 to 15

Each dentinal tubule sealant was prepared by weighing ingredients in a composition indicated in Tables 1 to 7 on an agate mortar so that the whole amount of a dentinal tubule sealant might be 20 g, and then kneading them with an agate pestle for 5 minutes. At this time, hydroxyapatite particles, a filler (B), sodium fluoride, and fumed silica did not change substantially in average particle diameter before and after mixing.

[Evaluation of Operability]

For the dentinal tubule sealants obtained in the above-mentioned preparation, operability was evaluated. The criteria for the operability evaluation are as follows.

A: The dentinal tubule sealant is a soft paste and it is easy to rub in a paste form into the dentin by the method using a rubber cup described below. Moreover, the paste can be washed away with water.

B: The dentinal tubule sealant is a firm paste and it can be rubbed in a paste form into the dentin by the method using a rubber cup described below. Moreover, the paste can be washed away with water.

C: The dentinal tubule sealant is so high in viscosity that it is difficult to rub in a paste form into the dentin by the method using a rubber cup described below.

The paste properties of A and B are preferable for use.

[Evaluation of Storage Stability]

A 5 g portion of the dentinal tubule sealant obtained in the above-mentioned preparation was placed in a screw vial made of glass, and then was left at rest at 37° C. for 24 hours. The storage stability was rated as B if the paste was cured in the glass screw vial after 24 hours, and the storage stability was rated as A if the paste was not cured and the state of the paste was maintained.

[Evaluation of Dentinal Tubule Sealing Ratio]

(1) Preparation of Bovine Tooth for Dentinal Tubule Sealing Ratio Evaluation

A cheek-side center of a healthy bovine incisor tooth was trimmed with #80, #1000 sand paper by using a rotary grinder, so that a 2-mm thick dentin plate with a cheek-side dentin exposed was produced. This cheek-side dentin surface was further polished with lapping films (#1200, #3000, #8000, manufactured by Sumitomo 3M Ltd.) to be smoothened. Lines were drawn on this cheek-side dentin part with a pencil (2B, Mitsubishi Pencil Co., Ltd.) to form a test part window sized to 14 mm in the longitudinal direction of the tooth and 8 mm in the lateral direction of the tooth (hereinafter sometimes called "dentin window"), and lines were further drawn also in the lateral direction of the tooth in order to divide the test part window into an upper part and a lower part (hereinafter, the upper window and the lower window are sometimes called "dentinal tubule sealing-untreated surface" and "dentinal tubule sealing-treated surface," respectively). As to this bovine tooth, a solution prepared by diluting a 0.5-M EDTA solution (manufactured by Wako Pharmaceutical) five times was applied to the dentin window for 30 seconds to perform demineralization, followed by washing with water for 30 minutes or more, and thus a bovine tooth used for evaluation of dentinal tubule sealing ratio was prepared.

(2) Preparation of Sample for Evaluation of Dentinal Tubule Sealing Ratio (Initial)

Onto the above-mentioned dentinal tubule sealing-treated surface, 0.1 g of a pasty dentinal tubule sealant with a composition indicated in Tables 1 to 7 was rubbed for 30 seconds at a rotation speed of 1500 rpm using a cordless handpiece for PMTC (Merssage PRO, manufactured by SHOFU INC.) and a rubber cup (MERSSAGE CUP No. 12, manufactured by SHOFU INC.). Then, the paste on the dentin surface was removed with distilled water. Following the treatment, the bovine tooth sample was placed into a plastic vial and the sample treated under reduced pressure for 1 hour was designated as a sample for evaluation of dentinal tubule sealing ratio (initial).

(3) Preparation of Artificial Saliva

Sodium chloride (8.77 g, 150 mmol), monopotassium dihydrogen phosphate (122 mg, 0.9 mmol), calcium chloride (166 mg, 1.5 mmol), and Hepes (4.77 g, 20 mmol) were separately weighed out on weighing dishes and then added one after another under stirring to a 2000-ml beaker containing about 800 ml of distilled water. After confirmation of complete dissolution of the solutes, pH was adjusted to 7.0 by dropping a 10% aqueous sodium hydroxide solution while measuring the acidity of the solution with a pH meter (F55, manufactured by HORIBA, Ltd.). Subsequently, this solution was added to a 1000-ml volumetric flask and diluted, so that 1000 ml of artificial saliva was obtained.

(4) Preparation of Sample for Evaluation of Dentinal Tubule Sealing Ratio (after Immersion in Artificial Saliva)

Onto the above-mentioned dentinal tubule sealing-treated surface, 0.1 g of a pasty dentinal tubule sealant with a composition indicated in Tables 1 to 7 was rubbed for 30 seconds at a rotation speed of 1500 rpm using a cordless handpiece for PMTC (Merssage PRO, manufactured by SHOFU INC.) and a rubber cup (MERSSAGE CUP No. 12, manufactured by SHOFU INC.). Then, the paste remaining on the dentin surface was removed with distilled water, and then the sample was immersed in the artificial saliva obtained in (3) above for one month. Following the treatment, the bovine tooth sample was placed into a plastic vial and the sample treated under reduced pressure for 1 hour was designated as a sample for evaluation of dentinal tubule sealing ratio (after immersion in artificial saliva).

(5) SEM Observation

An electron microscope (S-3500N, manufactured by Hitachi High-Tech Fielding Corporation) was used for SEM observation. For the samples obtained in (2) and (4) above, the conditions of a dentinal tubule sealing-untreated surface and a dentinal tubule sealing-treated surface were observed at an accelerating voltage of 15 kV, and it was confirmed that no sealing material was observed in dentinal tubules in the dentinal tubule sealing-untreated surface at 3000 magnifications. Then, three photographs of the dentinal tubule sealing-treated surface were taken. For each of the three photographs obtained, the number of all dentinal tubules and the number of dentinal tubules sealed were counted by visual observation, and then a dentinal tubule sealing ratio was calculated according to the following formula.

Dentinal tubule sealing ratio (%)=[(number of dentinal tubules sealed)/(total number of dentinal tubules)]×100

(6) Increase of Dentinal Tubule Sealing Ratio

A value obtained by subtracting a dentinal tubule sealing ratio (initial) from a dentinal tubule sealing ratio (after immersion in artificial saliva) was defined as an increase of dentinal tubule sealing ratio.

[Dentin Penetration Inhibition Ratio Evaluation]

(1) Preparation of Bovine Tooth for Dentin Penetration Inhibition Ratio Evaluation A cheek-side dentin of a healthy bovine incisor tooth was trimmed with #80, #1000 sand paper by using a rotary grinder, and thus a bovine tooth disc being about 1.5 cm in diameter and 0.9 mm in thickness was produced. This bovine tooth disc surface was further polished with lapping films (#1200, #3000, #8000, manufactured by Sumitomo 3M Ltd.) to a thickness of 0.7 mm and thus was smoothened. This bovine tooth disc was immersed for 180 seconds in a solution prepared by diluting 5 times a 0.5 M EDTA solution (manufactured by Wako Pure Chemical Industries, Ltd.), and then washed in distilled water for about 30 seconds and washed with distilled water for about 30 minutes, and thus a bovine tooth disc used for dentin penetration inhibition ratio evaluation was prepared.

(2) Preparation of Sample for Evaluation of Dentin Penetration Inhibition Ratio (Initial)

Onto the above-mentioned cheek-side dentin surface of the bovine tooth disc, 0.1 g of a pasty dentinal tubule sealant with a composition indicated in Tables 1 to 7 was rubbed for 30 seconds at a rotation speed of 1500 rpm using a cordless handpiece for PMTC (Merssage PRO, manufactured by SHOFU INC.) and a rubber cup (MERSSAGE CUP No. 12, manufactured by SHOFU INC.). Then, the paste on the dentin surface was removed with distilled water, and a dentin penetration inhibition ratio (initial) evaluation test (n=5) was carried out immediately.

(3) Preparation of Sample for Evaluation of Dentin Penetration Inhibition Ratio (Long Term)

Onto the above-mentioned cheek-side dentin surface of the bovine tooth disc, 0.1 g of a pasty dentinal tubule sealant with a composition indicated in Tables 1 to 7 was rubbed for 30 seconds at a rotation speed of 1500 rpm using a cordless handpiece for PMTC (Merssage PRO, manufactured by SHOFU INC.) and a rubber cup (MERSSAGE CUP No. 12, manufactured by SHOFU INC.). Then, the paste on the dentin surface was removed with distilled water, followed by immersion in the artificial saliva obtained in the above (3) of [Evaluation of dentinal tubule sealing ratio] for one month, and then a dentin penetration inhibition ratio (long term) evaluation test (n=5) was carried out.

(4) Dentin Penetration Inhibition Ratio Evaluation Test

The measurement of a dentin penetration inhibition ratio was carried out using a method according to the method of Pashley et al. (D. H. PASHLEY et al., J. Dent. Res. 65:417-420, 1986; K. C. Y. TAY et al., J. Endod. 33:1438-1443, 2007). The same device was installed, and the bovine tooth disc having been subjected to the dentinal tubule sealing treatment was installed and fixed to a dividable chamber jig so that a liquid could penetrate in a direction from the dental pulp toward the enamel. The dentin surface to receive pressure of Phosphate-buffered saline (Dulbecco's PBS, Grand Island Biological Company, Grand Island, N.Y.) was standardized to have a surface area of 78.5 $mm^2$ (5 mm in diameter) using an O ring and was pressurized at 10 psi (69 kPa), and then a penetrated amount was measured after a lapse of 24 hours. Moreover, a dentin penetration inhibition ratio was calculated using the following formula from the measurement of the penetrated amount for the same bovine tooth disc having not been subjected to the dentinal tubule sealing treatment by the same operation.

Dentin penetration inhibition ratio (%)=[1−(penetrated amount for dentinal tubule-sealed bovine tooth disc)/(penetrated amount for dentinal tubule-unsealed bovine tooth disc)]×100

(5) Increase of Dentin Penetration Inhibition Ratio

A value obtained by subtracting a dentin penetration inhibition ratio (initial) from a dentin penetration inhibition ratio (long term) was defined as an increase of penetration inhibition ratio.

TABLE 1

| | | Raw materials | Example 1 | Example 2 | Example 3 | Example 4 | Example 5 | Example 6 | Example 7 | Example 8 |
|---|---|---|---|---|---|---|---|---|---|---|
| Apatite particles (A) | | Hydroxyapatite (D50: 40 nm) (part(s) by weight) | | | | | | | | |
| | | Hydroxyapatite (D50: 150 nm) (part(s) by weight) | 72.7 | 40 | 7.3 | 63.6 | 52.5 | 35 | 17.5 | 6.4 |
| | | Hydroxyapatite (D50: 400 nm) (part(s) by weight) | | | | | | | | |
| Filler (B) | b2 | DCPA (D50: 0.5 μm) (part(s) by weight) | | | | | | | | |
| | b2 | DCPA (D50: 1 μm) (part(s) by weight) | | | | | | | | |
| | b2 | DCPA (D50: 2 μm) (part(s) by weight) | 7.3 | 40 | 72.7 | 6.4 | 17.5 | 35 | 52.5 | 63.6 |
| | b2 | DCPA (D50: 8 μm) (part(s) by weight) | | | | | | | | |
| | b1 | TTCP (D50: 2 μm) (part(s) by weight) | | | | | | | | |
| | b1 | Hydroxyapatite (D50: 2 μm) (part(s) by weight) | | | | | | | | |
| | b2 | α-TCP (D50: 2 μm) (part(s) by weight) | | | | | | | | |
| | b3 | Calcium carbonate (D50: 2 μm) (part(s) by weight) | | | | | | | | |
| | b3 | Calcium hydroxide (D50: 2 μm) (part(s) by weight) | | | | | | | | |
| | b3 | Calcium silicate (D50: 2 μm) (part(s) by weight) | | | | | | | | |
| | b4 | Ba glass (D50: 2 μm) (part(s) by weight) | | | | | | | | |
| | b4 | FAS glass (D50: 2 μm) (part(s) by weight) | | | | | | | | |
| | b4 | Zirconia (D50: 2 μm) (part(s) by weight) | | | | | | | | |
| | b' | Melamine resin (D50: 2 μm) (part(s) by weight) | | | | | | | | |
| Fluorine compound | | NaF (part(s) by weight) | | 0.1 | | | | | | |
| Thickener | | Ar-130 (part(s) by weight) | | | | | | | | |
| | | Ar-380 (part(s) by weight) | | | | | | | | |
| Dispersant (C) | | MACROGOL 400 (part(s) by weight) | | | | | | | | |
| | | MACROGOL 4000 (part(s) by weight) | | | | | | | | |
| | | Glycerol (part(s) by weight) | 20 | 19.9 | 20 | 30 | 30 | 30 | 30 | 30 |
| | | Water (part(s) by weight) | | | | | | | | |
| | | Total (part(s) by weight) | 100 | 100 | 100 | 100 | 100 | 100 | 100 | 100 |
| | | A/B | 10 | 1 | 0.1 | 10 | 3 | 1 | 0.33 | 0.1 |
| | | (A + B + C) relative to 100 parts by weight of dentinal tubule sealant (part(s) by weight) | 100 | 99.9 | 100 | 100 | 100 | 100 | 100 | 100 |
| | | C relative to 100 parts by weight of dentinal tubule sealant (part(s) by weight) | 20 | 19.9 | 20 | 30 | 30 | 30 | 30 | 30 |
| | | Operability | B | B | B | B | B | B | B | B |
| | | Initial dentinal tubule sealing ratio (%) | 71.1 | 72.1 | 73.1 | 62.1 | 65.4 | 69.4 | 67.1 | 63.3 |
| | | Dentinal tubule sealing ratio (%) after one-month immersion in saliva | 89.7 | 90.2 | 91.3 | 79.0 | 83.2 | 93.3 | 84.1 | 78.3 |
| | | Increase of sealing ratio | 18.6 | 18.1 | 18.2 | 16.9 | 17.8 | 23.9 | 17.0 | 15.0 |
| | | Penetration inhibition ratio (%) immediately after treatment | 71.1 | 72.1 | 73.1 | 62.1 | 65.4 | 69.4 | 67.1 | 63.3 |
| | | Penetration inhibition ratio (%) after one-month immersion in saliva | 89.7 | 90.2 | 91.3 | 79.0 | 83.2 | 93.3 | 84.1 | 78.3 |
| | | Increase of penetration inhibition ratio | 18.6 | 18.1 | 18.2 | 16.9 | 17.8 | 23.9 | 17.0 | 15.0 |
| | | Storage stability | A | A | A | A | A | A | A | A |

| | | Raw materials | Example 9 | Example 10 | Example 11 | Example 12 | Example 13 | Example 14 | Example 15 | Example 16 |
|---|---|---|---|---|---|---|---|---|---|---|
| Apatite particles (A) | | Hydroxyapatite (D50: 40 nm) (part(s) by weight) | | | | | | | | |
| | | Hydroxyapatite (D50: 150 nm) (part(s) by weight) | 30 | 10 | 9.1 | 7.5 | 5 | 2.5 | 0.9 | 2.5 |
| | | Hydroxyapatite (D50: 400 nm) (part(s) by weight) | | | | | | | | |
| Filler (B) | b2 | DCPA (D50: 0.5 μm) (part(s) by weight) | | | | | | | | |
| | b2 | DCPA (D50: 1 μm) (part(s) by weight) | | | | | | | | |

TABLE 1-continued

| | | Raw materials | | | | | | | | |
|---|---|---|---|---|---|---|---|---|---|---|
| | b2 | DCPA (D50: 2 μm) (part(s) by weight) | 30 | 10 | 0.9 | 2.5 | 5 | 7.5 | 9.1 | 2.5 |
| | b2 | DCPA (D50: 8 μm) (part(s) by weight) | | | | | | | | |
| | b1 | TTCP (D50: 2 μm) (part(s) by weight) | | | | | | | | |
| | b1 | Hydroxyapatite (D50: 2 μm) (part(s) by weight) | | | | | | | | |
| | b2 | α-TCP (D50: 2 μm) (part(s) by weight) | | | | | | | | |
| | b3 | Calcium carbonate (D50: 2 μm) (part(s) by weight) | | | | | | | | |
| | b3 | Calcium hydroxide (D50: 2 μm) (part(s) by weight) | | | | | | | | |
| | b3 | Calcium silicate (D50: 2 μm) (part(s) by weight) | | | | | | | | |
| | b4 | Ba glass (D50: 2 μm) (part(s) by weight) | | | | | | | | |
| | b4 | FAS glass (D50: 2 μm) (part(s) by weight) | | | | | | | | |
| | b4 | Zirconia (D50: 2 μm) (part(s) by weight) | | | | | | | | |
| | b' | Melamine resin (D50. 2 μm) (part(s) by weight) | | | | | | | | |
| Fluorine compound | | NaF (part(s) by weight) | | | | | | | | |
| Thickener | | Ar-130 (part(s) by weight) | 2 | | | | | | | |
| | | Ar-380 (part(s) by weight) | | 2.5 | 5 | 5 | 5 | 5 | 5 | 5 |
| Dispersant (C) | | MACROGOL 400 (part(s) by weight) | | 25 | 25 | 25 | 25 | 25 | 25 | 27.5 |
| | | MACROGOL 4000 (part(s) by weight) | | 10 | 10 | 10 | 10 | 10 | 10 | 12.5 |
| | | Glycerol (part(s) by weight) | 38 | 42.5 | 50 | 50 | 50 | 50 | 50 | 50 |
| | | Water (part(s) by weight) | | | | | | | | |
| | | Total (part(s) by weight) | 100 | 100 | 100 | 100 | 100 | 100 | 100 | 100 |
| | | A/B | 1 | 1 | 10 | 3 | 1 | 0.33 | 0.1 | 1 |
| | | (A + B + C) relative to 100 parts by weight of dentinal tubule sealant (part(s) by weight) | 98 | 97.5 | 95 | 95 | 95 | 95 | 95 | 95 |
| | | C relative to 100 parts by weight of dentinal tubule sealant | 38 | 77.5 | 85 | 85 | 85 | 85 | 85 | 90 |
| | | Operability | B | A | A | A | A | A | A | A |
| | | Initial dentinal tubule sealing ratio (%) | 60.1 | 58.6 | 55.4 | 56.8 | 58.9 | 55.8 | 55.8 | 52.1 |
| | | Dentinal tubule sealing ratio (%) after one-month immersion in saliva | 77.7 | 77.2 | 72.1 | 74.0 | 82.6 | 73.1 | 72.5 | 68.8 |
| | | Increase of sealing ratio | 17.6 | 18.6 | 16.7 | 17.2 | 23.7 | 17.3 | 16.7 | 16.7 |
| | | Penetration inhibition ratio (%) immediately after treatment | 60.1 | 58.6 | 55.4 | 56.8 | 58.9 | 55.8 | 55.8 | 52.1 |
| | | Penetration inhibition ratio (%) after one-month immersion in saliva | 77.7 | 77.2 | 72.1 | 74.0 | 82.6 | 73.1 | 72.5 | 68.8 |
| | | Increase of penetration inhibition ratio | 17.6 | 18.6 | 16.7 | 17.2 | 23.7 | 17.3 | 16.7 | 16.7 |
| | | Storage stability | A | A | A | A | A | A | A | A |

TABLE 2

| | | Raw materials | Example 17 | Example 18 | Example 19 | Example 20 | Example 21 | Example 22 | Example 23 | Example 24 |
|---|---|---|---|---|---|---|---|---|---|---|
| Apatite particles (A) | | Hydroxyapatite (D50: 40 nm) (part(s) by weight) | 35 | | 5 | | | | | |
| | | Hydroxyapatite (D50: 150 nm) (part(s) by weight) | | | | | 35 | 35 | 5 | 5 |
| | | Hydroxyapatite (D50: 400 nm) (part(s) by weight) | | 35 | | 5 | | | | |
| Filler (B) | b2 | DCPA (D50: 0.5 μm) (part(s) by weight) | | | | | | | | |
| | b2 | DCPA (D50: 1 μm) (part(s) by weight) | | | | | 35 | | 5 | |
| | b2 | DCPA (D50: 2 μm) (part(s) by weight) | 35 | 35 | 5 | 5 | | | | |
| | b2 | DCPA (D50: 8 μm) (part(s) by weight) | | | | | | 35 | | 5 |
| | b1 | TTCP (D50: 2 μm) (part(s) by weight) | | | | | | | | |
| | b1 | Hydroxyapatite (D50: 2 μm) (part(s) by weight) | | | | | | | | |

TABLE 2-continued

|  |  | | | | | | | | |
|---|---|---|---|---|---|---|---|---|---|
| | b2 | α-TCP (D50: 2 μm) (part(s) by weight) | | | | | | | |
| | b3 | Calcium carbonate (D50: 2 μm) (part(s) by weight) | | | | | | | |
| | b3 | Calcium hydroxide (D50: 2 μm) (part(s) by weight) | | | | | | | |
| | b3 | Calcium silicate (D50: 2 μm) (part(s) by weight) | | | | | | | |
| | b4 | Ba glass (D50: 2 μm) (part(s) by weight) | | | | | | | |
| | b4 | FAS glass (D50: 2 μm) (part(s) by weight) | | | | | | | |
| | b4 | Zirconia (D50: 2 μm) (part(s) by weight) | | | | | | | |
| | b' | Melamine resin (D50: 2 μm) (part(s) by weight) | | | | | | | |
| Fluorine compound | | NaF (part(s) by weight) | | | | | | | |
| Thickener | | Ar-130 (part(s) by weight) | | | | | | | |
| | | Ar-380 (part(s) by weight) | | 5 | 5 | | | 5 | 5 |
| Dispersant (C) | | MACROGOL 400 (part(s) by weight) | | 25 | 25 | | | 25 | 25 |
| | | MACROGOL 4000 (part(s) by weight) | | 10 | 10 | | | 10 | 10 |
| | | Glycerol (part(s) by weight) | 30 | 30 | 50 | 50 | 30 | 30 | 50 | 50 |
| | | Water (part(s) by weight) | | | | | | | | |
| | | Total (part(s) by weight) | 100 | 100 | 100 | 100 | 100 | 100 | 100 | 100 |
| | | A/B | 1 | 1 | 1 | 1 | 1 | 1 | 1 | 1 |
| | | (A + B + C) relative to 100 parts by weight of dentinal tubule sealant (part(s) by weight) | 100 | 100 | 95 | 95 | 100 | 100 | 95 | 95 |
| | | C relative to 100 parts by weight of dentinal tubule sealant (part(s) by weight) | 30 | 30 | 85 | 85 | 30 | 30 | 85 | 85 |
| | | Operability | B | B | A | A | B | B | A | A |
| | | Initial dentinal tubule sealing ratio (%) | 65.4 | 65.3 | 55.7 | 58.9 | 65.3 | 56.7 | 55.9 | 56.9 |
| | | Dentinal tubule sealing ratio (%) after one-month immersion in saliva | 88.1 | 85.2 | 74.6 | 76.6 | 85.2 | 74.6 | 73.6 | 75.5 |
| | | Increase of sealing ratio | 22.7 | 19.9 | 18.9 | 17.7 | 19.9 | 17.9 | 17.7 | 18.6 |
| | | Penetration inhibition ratio (%) immediately after treatment | 65.4 | 65.3 | 55.7 | 58.9 | 65.3 | 56.7 | 55.9 | 56.9 |
| | | Penetration inhibition ratio (%) after one-month immersion in saliva | 88.1 | 85.2 | 74.6 | 76.6 | 85.2 | 74.6 | 73.6 | 75.5 |
| | | Increase of penetration inhibition ratio | 22.7 | 19.9 | 18.9 | 17.7 | 19.9 | 17.9 | 17.7 | 18.6 |
| | | Storage stability | A | A | A | A | A | A | A | A |

| | | Raw materials | Example 25 | Example 26 | Example 27 | Example 28 | Example 29 | Example 30 | Example 31 | Example 32 |
|---|---|---|---|---|---|---|---|---|---|
| Apatite particles (A) | | Hydroxyapatite (D50: 40 nm) (part(s) by weight) | | | | | | | | |
| | | Hydroxyapatite (D50: 150 nm) (part(s) by weight) | 35 | 5 | 35 | 5 | 35 | 5 | 35 | 5 |
| | | Hydroxyapatite (D50: 400 nm) (part(s) by weight) | | | | | | | | |
| Filler (B) | b2 | DCPA (D50: 0.5 μm) (part(s) by weight) | | | | | | | | |
| | b2 | DCPA (D50: 1 μm) (part(s) by weight) | | | | | | | | |
| | b2 | DCPA (D50: 2 μm) (part(s) by weight) | | | | | | | | |
| | b2 | DCPA (D50: 8 μm) (part(s) by weight) | | | | | | | | |
| | b1 | TTCP (D50: 2 μm) (part(s) by weight) | 35 | 5 | | | | | | |
| | b1 | Hydroxyapatite (D50: 2 μm) (part(s) by weight) | | | | | | | | |
| | b2 | α-TCP (D50: 2 μm) (part(s) by weight) | | | 35 | 5 | | | | |
| | b3 | Calcium carbonate (D50: 2 μm) (part(s) by weight) | | | | | 35 | 5 | | |
| | b3 | Calcium hydroxide (D50: 2 μm) (part(s) by weight) | | | | | | | | |
| | b3 | Calcium silicate (D50: 2 μm) (part(s) by weight) | | | | | | | | |
| | b4 | Ba glass (D50: 2 μm) (part(s) by weight) | | | | | | | | |
| | b4 | FAS glass (D50: 2 μm) (part(s) by weight) | | | | | | | 35 | 5 |
| | b4 | Zirconia (D50: 2 μm) (part(s) by weight) | | | | | | | | |

TABLE 2-continued

|  |  |  |  |  |  |  |  |  |  |
|---|---|---|---|---|---|---|---|---|---|
|  | b' | Melamine resin (D50: 2 μm) (part(s) by weight) |  |  |  |  |  |  |  |
| Fluorine compound |  | NaF (part(s) by weight) |  |  |  |  |  |  |  |
| Thickener |  | Ar-130 (part(s) by weight) |  |  |  |  |  |  |  |
|  |  | Ar-380 (part(s) by weight) | 5 | 5 | 5 | 5 |  |  |  |
| Dispersant (C) |  | MACROGOL 400 (part(s) by weight) | 25 | 25 | 25 | 25 |  |  |  |
|  |  | MACROGOL 4000 (part(s) by weight) | 10 | 10 | 10 | 10 |  |  |  |
|  |  | Glycerol (part(s) by weight) | 30 | 50 | 30 | 50 | 30 | 50 | 30 | 50 |
|  |  | Water (part(s) by weight) |  |  |  |  |  |  |  |  |
|  |  | Total (part(s) by weight) | 100 | 100 | 100 | 100 | 100 | 100 | 100 | 100 |
|  |  | A/B | 1 | 1 | 1 | 1 | 1 | 1 | 1 | 1 |
| (A + B + C) relative to 100 parts by weight of dentinal tubule sealant (part(s) by weight) |  |  | 100 | 95 | 100 | 95 | 100 | 95 | 100 | 95 |
| C relative to 100 parts by weight of dentinal tubule sealant (part(s) by weight) |  |  | 30 | 85 | 30 | 85 | 30 | 85 | 30 | 85 |
|  |  | Operability | B | A | B | A | B | A | B | A |
|  |  | Initial dentinal tubule sealing ratio (%) | 67.4 | 58.9 | 66.7 | 58.9 | 68.4 | 59.0 | 66.3 | 57.8 |
|  |  | Dentinal tubule sealing ratio (%) after one-month immersion in saliva | 91.3 | 83.6 | 90.4 | 82.1 | 91.4 | 82.1 | 79.5 | 70.1 |
|  |  | Increase of sealing ratio | 23.9 | 24.7 | 23.7 | 23.2 | 23.0 | 23.1 | 13.2 | 12.3 |
|  |  | Penetration inhibition ratio (%) immediately after treatment | 67.4 | 58.9 | 66.7 | 58.9 | 68.4 | 59.0 | 66.3 | 57.8 |
|  |  | Penetration inhibition ratio (%) after one-month immersion in saliva | 91.3 | 83.6 | 90.4 | 82.1 | 91.4 | 82.1 | 79.5 | 70.1 |
|  |  | Increase of penetration inhibition ratio | 23.9 | 24.7 | 23.7 | 23.2 | 23.0 | 23.1 | 13.2 | 12.3 |
|  |  | Storage stability | A | A | A | A | A | A | A | A |

TABLE 3

|  |  | Raw materials | Example 33 | Example 34 | Example 35 | Example 36 | Example 37 | Example 38 | Example 39 | Example 40 |
|---|---|---|---|---|---|---|---|---|---|---|
| Apatite particles (A) |  | Hydroxyapatite (D50: 40 nm) (part(s) by weight) |  |  |  |  |  |  |  |  |
|  |  | Hydroxyapatite (D50: 150 nm) (part(s) by weight) | 35 | 5 | 35 | 5 | 35 | 35 | 35 | 5 |
|  |  | Hydroxyapatite (D50: 400 nm) (part(s) by weight) |  |  |  |  |  |  |  |  |
| Filler (B) | b2 | DCPA (D50: 0.5 μm) (part(s) by weight) |  |  |  |  |  |  |  |  |
|  | b2 | DCPA (D50: 1 μm) (part(s) by weight) |  |  |  |  |  |  |  |  |
|  | b2 | DCPA (D50: 2 μm) (part(s) by weight) |  |  |  |  | 29.7 | 9.5 | 20.1 | 1.4 |
|  | b2 | DCPA (D50: 8 μm) (part(s) by weight) |  |  |  |  |  |  |  |  |
|  | b1 | TTCP (D50: 2 μm) (part(s) by weight) |  |  |  |  | 5.3 | 25.5 | 14.9 | 3.6 |
|  | b1 | Hydroxyapatite (D50: 2 μm) (part(s) by weight) |  |  |  |  |  |  |  |  |
|  | b2 | α-TCP (D50: 2 μm) (part(s) by weight) |  |  |  |  |  |  |  |  |
|  | b3 | Calcium carbonate (D50: 2 μm) (part(s) by weight) |  |  |  |  |  |  |  |  |
|  | b3 | Calcium hydroxide (D50: 2 μm) (part(s) by weight) |  |  |  |  |  |  |  |  |
|  | b3 | Calcium silicate (D50: 2 μm) (part(s) by weight) |  |  |  |  |  |  |  |  |
|  | b4 | Ba glass (D50: 2 μm) (part(s) by weight) | 35 | 5 |  |  |  |  |  |  |
|  | b4 | FAS glass (D50: 2 μm) (part(s) by weight) |  |  |  |  |  |  |  |  |
|  | b4 | Zirconia (D50: 2 μm) (part(s) by weight) |  |  |  |  |  |  |  |  |
|  | b' | Melamine resin (D50: 2 μm) (part(s) by weight) |  |  | 35 | 5 |  |  |  |  |
| Fluorine compound |  | NaF (part(s) by weight) |  |  |  |  |  |  |  |  |
| Thickener |  | Ar-130 (part(s) by weight) |  |  |  |  |  |  |  |  |
|  |  | Ar-380 (part(s) by weight) | 5 | 5 |  |  |  |  |  | 5 |

TABLE 3-continued

|  |  |  |  |  |  |  |  |  |  |
|---|---|---|---|---|---|---|---|---|---|
| Dispersant (C) | MACROGOL 400 (part(s) by weight) |  | 25 |  | 25 |  |  |  | 25 |
|  | MACROGOL 4000 (part(s) by weight) |  | 10 |  | 10 |  |  |  | 10 |
|  | Glycerol (part(s) by weight) | 30 | 50 | 30 | 50 | 30 | 30 | 30 | 50 |
|  | Water (part(s) by weight) |  |  |  |  |  |  |  |  |
| Total (part(s) by weight) |  | 100 | 100 | 100 | 100 | 100 | 100 | 100 | 100 |
| A/B |  | 1 | 1 | 1 | 1 | 1 | 1 | 1 | 1 |
| (A + B + C) relative to 100 parts by weight of dentinal tubule sealant (part(s) by weight) |  | 100 | 95 | 100 | 95 | 100 | 100 | 100 | 95 |
| C relative to 100 parts by weight of dentinal tubule sealant (part(s) by weight) |  | 30 | 85 | 30 | 85 | 30 | 30 | 30 | 85 |
| Operability |  | B | A | B | A | B | B | B | A |
| Initial dentinal tubule sealing ratio (%) |  | 65.5 | 55.9 | 67.4 | 58.5 | 71.3 | 71.3 | 70.3 | 64.3 |
| Dentinal tubule sealing ratio (%) after one-month immersion in saliva |  | 75.5 | 67.0 | 70.6 | 62.5 | 94.5 | 94.9 | 93.6 | 89.1 |
| Increase of sealing ratio |  | 10.0 | 11.1 | 3.2 | 4.0 | 23.2 | 23.6 | 23.3 | 24.8 |
| Penetration inhibition ratio (%) immediately after treatment |  | 65.5 | 55.9 | 67.4 | 58.5 | 71.3 | 71.3 | 70.3 | 64.3 |
| Penetration inhibition ratio (%) after one-month immersion in saliva |  | 75.5 | 67.0 | 70.6 | 62.5 | 94.5 | 94.9 | 93.6 | 88.1 |
| Increase of penetration inhibition ratio |  | 10.0 | 11.1 | 3.2 | 4.0 | 23.2 | 23.6 | 23.3 | 23.8 |
| Storage stability |  | A | A | A | A | A | A | A | A |

|  | Raw materials | Example 41 | Example 42 | Example 43 | Example 44 | Example 45 | Example 46 | Example 47 | Example 48 |
|---|---|---|---|---|---|---|---|---|---|
| Apatite particles (A) | Hydroxyapatite (D50: 40 nm) (part(s) by weight) |  |  |  |  |  |  |  |  |
|  | Hydroxyapatite (D50: 150 nm) (part(s) by weight) | 35 | 5 | 35 | 35 | 35 | 5 | 35 | 5 |
|  | Hydroxyapatite (D50: 400 nm) (part(s) by weight) |  |  |  |  |  |  |  |  |
| Filler (B) | b2 DCPA (D50: 0.5 μm) (part(s) by weight) |  |  |  |  |  |  |  |  |
|  | b2 DCPA (D50: 1 μm) (part(s) by weight) |  |  |  |  |  |  |  |  |
|  | b2 DCPA (D50: 2 μm) (part(s) by weight) |  |  | 4.5 | 23.5 | 20.2 | 3.4 | 25.7 | 3.7 |
|  | b2 DCPA (D50: 8 μm) (part(s) by weight) |  |  |  |  |  |  |  |  |
|  | b1 TTCP (D50: 2 μm) (part(s) by weight) | 13.2 | 1.9 |  |  |  |  |  |  |
|  | b1 Hydroxyapatite (D50: 2 μm) (part(s) by weight) |  |  |  |  |  |  |  |  |
|  | b2 α-TCP (D50: 2 μm) (part(s) by weight) | 21.8 | 3.1 |  |  |  |  |  |  |
|  | b3 Calcium carbonate (D50: 2 μm) (part(s) by weight) |  |  | 30.5 | 11.5 | 14.8 | 1.6 |  |  |
|  | b3 Calcium hydroxide (D50: 2 μm) (part(s) by weight) |  |  |  |  |  |  | 9.3 | 1.3 |
|  | b3 Calcium silicate (D50: 2 μm) (part(s) by weight) |  |  |  |  |  |  |  |  |
|  | b4 Ba glass (D50: 2 μm) (part(s) by weight) |  |  |  |  |  |  |  |  |
|  | b4 FAS glass (D50: 2 μm) (part(s) by weight) |  |  |  |  |  |  |  |  |
|  | b4 Zirconia (D50: 2 μm) (part(s) by weight) |  |  |  |  |  |  |  |  |
|  | b' Melamine resin (D50: 2 μm) (part(s) by weight) |  |  |  |  |  |  |  |  |
| Fluorine compound | NaF (part(s) by weight) |  |  |  |  |  |  |  | 0.1 |
| Thickener | Ar-130 (part(s) by weight) |  |  |  |  |  |  |  |  |
|  | Ar-380 (part(s) by weight) |  | 5 |  |  |  | 5 |  | 5 |
| Dispersant (C) | MACROGOL 400 (part(s) by weight) |  | 25 |  |  |  | 25 |  | 25 |
|  | MACROGOL 4000 (part(s) by weight) |  | 10 |  |  |  | 10 |  | 10 |
|  | Glycerol (part(s) by weight) | 30 | 50 | 30 | 30 | 30 | 50 | 29.9 | 50 |
|  | Water (part(s) by weight) |  |  |  |  |  |  |  |  |
| Total (part(s) by weight) |  | 100 | 100 | 100 | 100 | 100 | 100 | 100 | 100 |
| A/B |  | 1 | 1 | 1 | 1 | 1 | 1 | 1 | 1 |
| (A + B + C) relative to 100 parts by weight of dentinal tubule sealant (part(s) by weight) |  | 100 | 95 | 100 | 100 | 100 | 95 | 99.9 | 95 |
| C relative to 100 parts by weight of dentinal tubule sealant (part(s) by weight) |  | 30 | 85 | 30 | 30 | 30 | 85 | 29.9 | 85 |

TABLE 3-continued

|  |  |  |  |  |  |  |  |  |
|---|---|---|---|---|---|---|---|---|
| Operability | B | A | B | B | B | A | B | A |
| Initial dentinal tubule sealing ratio (%) | 70.6 | 60.1 | 71.2 | 70.3 | 70.9 | 63.9 | 71.5 | 61.2 |
| Dentinal tubule sealing ratio (%) after one-month immersion in saliva | 94.3 | 84.6 | 94.3 | 93.7 | 94.0 | 87.0 | 94.5 | 84.5 |
| Increase of sealing ratio | 23.7 | 24.5 | 23.1 | 23.4 | 23.1 | 23.1 | 23.0 | 23.3 |
| Penetration inhibition ratio (%) immediately after treatment | 70.6 | 60.1 | 71.2 | 70.3 | 70.9 | 63.9 | 70.1 | 61.2 |
| Penetration inhibition ratio (%) after one-month immersion in saliva | 94.3 | 83.6 | 94.3 | 93.7 | 93.9 | 86.9 | 92.9 | 85.1 |
| Increase of penetration inhibition ratio | 23.7 | 23.5 | 23.1 | 23.4 | 23.0 | 23.0 | 22.8 | 23.9 |
| Storage stability | A | A | A | A | A | A | A | A |

TABLE 4

|  | Raw materials | Example 49 | Example 50 | Example 51 | Example 52 | Example 53 | Example 54 | Example 55 |
|---|---|---|---|---|---|---|---|---|
| Apatite particles (A) | Hydroxyapatite (D50: 40 nm) (part(s) by weight) |  |  |  |  |  |  |  |
|  | Hydroxyapatite (D50: 150 nm) (part(s) by weight) | 35 | 5 | 35 | 5 | 35 | 5 | 35 |
|  | Hydroxyapatite (D50: 400 nm) (part(s) by weight) |  |  |  |  |  |  |  |
| Filler (B) b2 | DCPA (D50: 0.5 μm) (part(s) by weight) |  |  |  |  |  |  |  |
| b2 | DCPA (D50: 1 μm) (part(s) by weight) |  |  |  |  |  |  |  |
| b2 | DCPA (D50: 2 μm) (part(s) by weight) |  |  |  |  | 4.7 | 0.7 | 11.7 |
| b2 | DCPA (D50: 8 μm) (part(s) by weight) |  |  |  |  |  |  |  |
| b1 | TTCP (D50: 2 μm) (part(s) by weight) |  |  |  |  | 12.8 | 1.8 |  |
| b1 | Hydroxyapatite (D50: 2 μm) (part(s) by weight) |  |  |  |  |  |  |  |
| b2 | α-TCP (D50: 2 μm) (part(s) by weight) | 31.6 | 4.5 | 32.4 | 4.6 |  |  |  |
| b3 | Calcium carbonate (D50: 2 μm) (part(s) by weight) | 3.4 | 0.5 |  |  |  |  | 5.8 |
| b3 | Calcium hydroxide (D50: 2 μm) (part(s) by weight) |  |  | 2.6 | 0.4 |  |  |  |
| b3 | Calcium silicate (D50: 2 μm) (part(s) by weight) |  |  |  |  |  |  |  |
| b4 | Ba glass (D50: 2 μm) (part(s) by weight) |  |  |  |  |  |  |  |
| b4 | FAS glass (D50: 2 μm) (part(s) by weight) |  |  |  |  | 17.5 | 2.5 | 17.5 |
| b4 | Zirconia (D50: 2 μm) (part(s) by weight) |  |  |  |  |  |  |  |
| b' | Melamine resin (D50: 2 μm) (part(s) by weight) |  |  |  |  |  |  |  |
| Fluorine compound | NaF (part(s) by weight) |  |  |  |  |  |  |  |
| Thickener | Ar-130 (part(s) by weight) |  |  |  |  |  |  |  |
|  | Ar-380 (part(s) by weight) |  | 5 |  | 5 |  | 5 |  |
| Dispersant (C) | MACROGOL 400 (part(s) by weight) |  | 25 |  | 25 |  | 25 |  |
|  | MACROGOL 4000 (part(s) by weight) |  | 10 |  | 10 |  | 10 |  |
|  | Glycerol (part(s) by weight) | 30 | 50 | 30 | 50 | 30 | 50 | 30 |
|  | Water (part(s) by weight) |  |  |  |  |  |  |  |
|  | Total (part(s) by weight) | 100 | 100 | 100 | 100 | 100 | 100 | 100 |
|  | A/B | 1 | 1 | 1 | 1 | 1 | 1 | 1 |
|  | (A + B + C) relative to 100 parts by weight of dentinal tubule sealant (part(s) by weight) | 100 | 95 | 100 | 95 | 100 | 95 | 100 |
|  | C relative to 100 parts by weight of dentinal tubule sealant (part(s) by weight) | 30 | 85 | 30 | 85 | 30 | 85 | 30 |
|  | Operability | B | A | B | A | B | A | B |
|  | Initial dentinal tubule sealing ratio (%) | 70.4 | 60.0 | 70.2 | 60.8 | 70.4 | 57.8 | 70.1 |
|  | Dentinal tubule sealing ratio (%) after one-month immersion in saliva | 93.4 | 83.3 | 93.3 | 83.9 | 94.1 | 80.9 | 93.1 |
|  | Increase of sealing ratio | 23.0 | 23.3 | 23.1 | 23.1 | 23.7 | 23.1 | 23.0 |
|  | Penetration inhibition ratio (%) immediately after treatment | 70.4 | 61.5 | 70.2 | 60.8 | 69.9 | 60.0 | 70.3 |
|  | Penetration inhibition ratio (%) after one-month immersion in saliva | 93.5 | 84.0 | 93.2 | 83.3 | 94.3 | 84.1 | 94.0 |

TABLE 4-continued

| | | Increase of penetration inhibition ratio | 23.1 | 22.5 | 23.0 | 22.5 | 24.4 | 24.1 | 23.7 |
|---|---|---|---|---|---|---|---|---|---|
| | | Storage stability | A | A | A | A | A | A | A |

| | | Raw materials | Example 56 | Example 57 | Example 58 | Example 59 | Example 60 | Example 61 |
|---|---|---|---|---|---|---|---|
| Apatite particles (A) | | Hydroxyapatite (D50: 40 nm) (part(s) by weight) | | | | | | |
| | | Hydroxyapatite (D50: 150 nm) (part(s) by weight) | 5 | 35 | 5 | 35 | 5 | 35 |
| | | Hydroxyapatite (D50: 400 nm) (part(s) by weight) | | | | | | |
| Filler (B) | b2 | DCPA (D50: 0.5 μm) (part(s) by weight) | | | | | | |
| | b2 | DCPA (D50: 1 μm) (part(s) by weight) | | | | | | |
| | b2 | DCPA (D50: 2 μm) (part(s) by weight) | 1.7 | 7 | 1 | 14.4 | 2 | 1.8 |
| | b2 | DCPA (D50: μm) (part(s) by weight) | | | | | | |
| | b1 | TTCP (D50: 2 μm) (part(s) by weight) | | 26.3 | 3.7 | 14.4 | 2 | 22.8 |
| | b1 | Hydroxyapatite (D50: 2 μm) (part(s) by weight) | | | | | | |
| | b2 | α-TCP (D50: 2 μm) (part(s) by weight) | | | | | | |
| | b3 | Calcium carbonate (D50: 2 μm) (part(s) by weight) | 0.8 | 1.7 | 0.3 | 6.2 | 1 | 10.4 |
| | b3 | Calcium hydroxide (D50: 2 μm) (part(s) by weight) | | | | | | |
| | b3 | Calcium silicate (D50: 2 μm) (part(s) by weight) | | | | | | |
| | b4 | Ba glass (D50: 2 μm) (part(s) by weight) | | | | | | |
| | b4 | FAS glass (D50: 2 μm) (part(s) by weight) | 2.5 | | | | | |
| | b4 | Zirconia (D50: 2 μm) (part(s) by weight) | | | | | | |
| | b' | Melamine resin (D50: 2 μm) (part(s) by weight) | | | | | | |
| Fluorine compound | | NaF (part(s) by weight) | | | | | | |
| Thickener | | Ar-130 (part(s) by weight) | | | | | | |
| | | Ar-380 (part(s) by weight) | 5 | | 5 | | 5 | |
| Dispersant (C) | | MACROGOL 400 (part(s) by weight) | 25 | | 25 | | 25 | |
| | | MACROGOL 4000 (part(s) by weight) | 10 | | 10 | | 10 | |
| | | Glycerol (part(s) by weight) | 50 | 30 | 50 | 30 | 50 | 30 |
| | | Water (part(s) by weight) | | | | | | |
| | | Total (part(s) by weight) | 100 | 100 | 100 | 100 | 100 | 100 |
| | | A/B | 1 | 1 | 1 | 1 | 1 | 1 |
| | | (A + B + C) relative to 100 parts by weight of dentinal tubule sealant (part(s) by weight) | 95 | 100 | 95 | 100 | 95 | 100 |
| | | C relative to 100 parts by weight of dentinal tubule sealant (part(s) by weight) | 85 | 30 | 85 | 30 | 85 | 30 |
| | | Operability | A | B | A | B | A | B |
| | | Initial dentinal tubule sealing ratio (%) | 59.9 | 73.2 | 65.6 | 76.1 | 64.2 | 74.1 |
| | | Dentinal tubule sealing ratio (%) after one-month immersion in saliva | 86.9 | 98.1 | 89.4 | 99.4 | 88.1 | 98.1 |
| | | Increase of sealing ratio | 27.0 | 24.9 | 23.8 | 23.3 | 23.9 | 24.0 |
| | | Penetration inhibition ratio (%) immediately after treatment | 60.8 | 70.1 | 65.1 | 73.1 | 64.2 | 72.5 |
| | | Penetration inhibition ratio (%) after one-month immersion in saliva | 84.5 | 93.2 | 88.4 | 99.1 | 88.1 | 98.4 |
| | | Increase of penetration inhibition ratio | 23.7 | 23.1 | 23.3 | 26.0 | 23.9 | 25.9 |
| | | Storage stability | A | A | A | A | A | A |

| | | Raw materials | Example 62 | Example 63 | Example 64 | Example 65 | Example 66 | Example 67 |
|---|---|---|---|---|---|---|---|
| Apatite particles (A) | | Hydroxyapatite (D50: 40 nm) (part(s) by weight) | | | | | | |
| | | Hydroxyapatite (D50: 150 nm) (part(s) by weight) | 5 | 5 | 35 | 5 | 35 | 5 |
| | | Hydroxyapatite (D50: 400 nm) (part(s) by weight) | | | | | | |
| Filler (B) | b2 | DCPA (D50: 0.5 μm) (part(s) by weight) | | | | | | |
| | b2 | DCPA (D50: 1 μm) (part(s) by weight) | | | | | | |

TABLE 4-continued

| | | | | | | | |
|---|---|---|---|---|---|---|---|
| b2 | DCPA (D50: 2 μm) (part(s) by weight) | 0.3 | 2 | | | 7 | 1 |
| b2 | DCPA (D50: 8 μm) (part(s) by weight) | | | | | | |
| b1 | TTCP (D50: 2 μm) (part(s) by weight) | 3.2 | 2 | | | 7 | 1 |
| b1 | Hydroxyapatite (D50: 2 μm) (part(s) by weight) | | | 35 | 5 | 17.5 | 2.5 |
| b2 | α-TCP (D50: 2 μm) (part(s) by weight) | | | | | | |
| b3 | Calcium carbonate (D50: 2 μm) (part(s) by weight) | 1.5 | 1 | | | 3.5 | 0.5 |
| b3 | Calcium hydroxide (D50: 2 μm) (part(s) by weight) | | | | | | |
| b3 | Calcium silicate (D50: 2 μm) (part(s) by weight) | | | | | | |
| b4 | Ba glass (D50: 2 μm) (part(s) by weight) | | | | | | |
| b4 | FAS glass (D50: 2 μm) (part(s) by weight) | | | | | | |
| b4 | Zirconia (D50: 2 μm) (part(s) by weight) | | | | | | |
| b' | Melamine resin (D50: 2 μm) (part(s) by weight) | | | | | | |
| Fluorine compound | NaF (part(s) by weight) | | | | | | |
| Thickener | Ar-130 (part(s) by weight) | 5 | 14.5 | | 5 | | 5 |
| | Ar-380 (part(s) by weight) | | | | | | |
| Dispersant (C) | MACROGOL 400 (part(s) by weight) | 25 | 15 | | 25 | | 25 |
| | MACROGOL 4000 (part(s) by weight) | 10 | 3 | | 10 | | 10 |
| | Glycerol (part(s) by weight) | 50 | 57.5 | 30 | 50 | 30 | 50 |
| | Water (part(s) by weight) | | | | | | |
| | Total (part(s) by weight) | 100 | 100 | 100 | 100 | 100 | 100 |
| | A/B | 1 | 1 | 1 | 1 | 1 | 1 |
| | (A + B + C) relative to 100 parts by weight of dentinal tubule sealant (part(s) by weight) | 95 | 85.5 | 100 | 95 | 100 | 95 |
| | C relative to 100 parts by weight of dentinal tubule sealant (part(s) by weight) | 85 | 75.5 | 30 | 85 | 30 | 85 |
| | Operability | A | B | B | A | B | A |
| | Initial dentinal tubule sealing ratio (%) | 65.2 | 63.2 | 60.8 | 60.8 | 70.2 | 60.1 |
| | Dentinal tubule sealing ratio (%) after one-month immersion in saliva | 89.2 | 88.4 | 86.9 | 86.9 | 98.4 | 86.9 |
| | Increase of sealing ratio | 24.0 | 25.2 | 26.1 | 26.1 | 28.2 | 26.8 |
| | Penetration inhibition ratio (%) immediately after treatment | 63.4 | 62.2 | 60.8 | 60.8 | 73.2 | 60.8 |
| | Penetration inhibition ratio (%) after one-month immersion in saliva | 88.5 | 87.1 | 86.9 | 86.9 | 96.2 | 87.9 |
| | Increase of penetration inhibition ratio | 25.1 | 24.9 | 26.1 | 26.1 | 23.0 | 27.1 |
| | Storage stability | A | A | A | A | A | A |

TABLE 5

| | Raw materials | Example 68 | Example 69 | Example 70 | Example 71 | Example 72 | Example 73 |
|---|---|---|---|---|---|---|---|
| Apatite particles (A) | Hydroxyapatite (D50: 40 nm) (part(s) by weight) | | | | | | |
| | Hydroxyapatite (D50: 150 nm) (part(s) by weight) | 72.7 | 40 | 7.3 | 63.6 | 52.5 | 35 |
| | Hydroxyapatite (D50: 400 nm) (part(s) by weight) | | | | | | |
| Filler (B) | b2 DCPA (D50: 0.5 μm) (part(s) by weight) | | | | | | |
| | b2 DCPA (D50: 1 μm) (part(s) by weight) | | | | | | |
| | b2 DCPA (D50: 2 μm) (part(s) by weight) | 7.3 | 40 | 72.7 | 6.4 | 17.5 | 35 |
| | b2 DCPA (D50: 8 μm) (part(s) by weight) | | | | | | |
| | b1 TTCP (D50: 2 μm) (part(s) by weight) | | | | | | |
| | b1 Hydroxyapatite (D50: 2 μm) (part(s) by weight) | | | | | | |
| | b2 α-TCP (D50: 2 μm) (part(s) by weight) | | | | | | |

TABLE 5-continued

| | | Raw materials | | | | | | |
|---|---|---|---|---|---|---|---|---|
| | b3 | Calcium carbonate (D50: 2 μm) (part(s) by weight) | | | | | | |
| | b3 | Calcium hydroxide (D50: 2 μm) (part(s) by weight) | | | | | | |
| | b3 | Calcium silicate (D50: 2 μm) (part(s) by weight) | | | | | | |
| | b4 | Ba glass (D50: 2 μm) (part(s) by weight) | | | | | | |
| | b4 | FAS glass (D50: 2 μm) (part(s) by weight) | | | | | | |
| | b4 | Zirconia (D50: 2 μm) (part(s) by weight) | | | | | | |
| | b' | Melamine resin (D50: 2 μm) (part(s) by weight) | | | | | | |
| Fluorine compound | | NaF (part(s) by weight) | | | | | | |
| Thickener | | Ar-130 (part(s) by weight) | | | | | | |
| | | Ar-380 (part(s) by weight) | | | | | | |
| Dispersant (C) | | MACROGOL 400 (part(s) by weight) | | | | | | |
| | | MACROGOL 4000 (part(s) by weight) | | | | | | |
| | | Glycerol (part(s) by weight) | | | | | | |
| | | Water (part(s) by weight) | 20 | 20 | 20 | 30 | 30 | 30 |
| | | Total (part(s) by weight) | 100 | 100 | 100 | 100 | 100 | 100 |
| | | A/B | 10 | 1 | 0.1 | 10 | 3 | 1 |
| (A + B + C) relative to 100 parts by weight of dentinal tubule sealant (part(s) by weight) | | | 100 | 100 | 100 | 100 | 100 | 100 |
| C relative to 100 parts by weight of dentinal tubule sealant (part(s) by weight) | | | 20 | 20 | 20 | 30 | 30 | 30 |
| | | Operability | B | B | B | B | B | B |
| | | Initial dentinal tubule sealing ratio (%) | 70.2 | 71.2 | 73.5 | 62.3 | 65.6 | 69.5 |
| | | Dentinal tubule sealing ratio (%) after one-month immersion in saliva | 87.9 | 89.7 | 91.2 | 78.8 | 82.6 | 93.5 |
| | | Increase of sealing ratio | 17.7 | 18.5 | 17.7 | 16.5 | 17.0 | 24.0 |
| | | Penetration inhibition ratio (%) immediately after treatment | 70.2 | 71.2 | 73.5 | 62.3 | 65.6 | 69.5 |
| | | Penetration inhibition ratio (%) after one-month immersion in saliva | 87.9 | 89.7 | 91.2 | 78.8 | 82.6 | 93.5 |
| | | Increase of penetration inhibition ratio | 17.7 | 18.5 | 17.7 | 16.5 | 17.0 | 24.0 |
| | | Storage stability | A | A | A | A | A | A |

| | | Raw materials | Example 74 | Example 75 | Example 76 | Example 77 | Example 78 | Example 79 |
|---|---|---|---|---|---|---|---|---|
| Apatite particles (A) | | Hydroxyapatite (D50: 40 nm) (part(s) by weight) | | | | | | |
| | | Hydroxyapatite (D50: 150 nm) (part(s) by weight) | 17.5 | 6.4 | 30 | 10 | 9.1 | 7.5 |
| | | Hydroxyapatite (D50: 400 nm) (part(s) by weight) | | | | | | |
| Filler (B) | b2 | DCPA (D50: 0.5 μm) (part(s) by weight) | | | | | | |
| | b2 | DCPA (D50: 1 μm) (part(s) by weight) | | | | | | |
| | b2 | DCPA (D50: 2 μm) (part(s) by weight) | 52.5 | 63.6 | 30 | 10 | 0.9 | 2.5 |
| | b2 | DCPA (D50: 8 μm) (part(s) by weight) | | | | | | |
| | b1 | TTCP (D50: 2 μm) (part(s) by weight) | | | | | | |
| | b1 | Hydroxyapatite (D50: 2 μm) (part(s) by weight) | | | | | | |
| | b2 | α-TCP (D50: 2 μm) (part(s) by weight) | | | | | | |
| | b3 | Calcium carbonate (D50: 2 μm) (part(s) by weight) | | | | | | |
| | b3 | Calcium hydroxide (D50: 2 μm) (part(s) by weight) | | | | | | |
| | b3 | Calcium silicate (D50: 2 μm) (part(s) by weight) | | | | | | |
| | b4 | Ba glass (D50: 2 μm) (part(s) by weight) | | | | | | |
| | b4 | FAS glass (D50: 2 μm) (part(s) by weight) | | | | | | |
| | b4 | Zirconia (D50: 2 μm) (part(s) by weight) | | | | | | |
| | b' | Melamine resin (D50: 2 μm) (part(s) by weight) | | | | | | |

TABLE 5-continued

| | | | | | | | |
|---|---|---|---|---|---|---|---|
| Fluorine compound | NaF (part(s) by weight) | | | | | | |
| Thickener | Ar-130 (part(s) by weight) | | | 2 | | | |
| | Ar-380 (part(s) by weight) | | | | 2.5 | 5 | 5 |
| Dispersant (C) | MACROGOL 400 (part(s) by weight) | | | | 25 | 25 | 25 |
| | MACROGOL 4000 (part(s) by weight) | | | | 12.5 | 12.5 | 12.5 |
| | Glycerol (part(s) by weight) | | | | | | |
| | Water (part(s) by weight) | 30 | 30 | 38 | 40 | 47.5 | 47.5 |
| | 1 Total (part(s) by weight) | 100 | 100 | 100 | 100 | 100 | 100 |
| | A/B | 0.33 | 0.1 | 1 | 1 | 10 | 3 |
| (A + B + C) relative to 100 parts by weight of dentinal tubule sealant (part(s) by weight) | | 100 | 100 | 98 | 97.5 | 95 | 95 |
| C relative to 100 parts by weight of dentinal tubule sealant (part(s) by weight) | | 30 | 30 | 38 | 77.5 | 85 | 85 |
| | Operability | B | B | B | A | A | A |
| | Initial dentinal tubule sealing ratio (%) | 66.0 | 65.3 | 60.3 | 57.6 | 55.6 | 56.5 |
| Dentinal tubule sealing ratio (%) after one-month immersion in saliva | | 84.3 | 78.1 | 77.5 | 76.8 | 72.0 | 74.2 |
| | Increase of sealing ratio | 18.3 | 12.8 | 17.2 | 19.2 | 16.4 | 17.7 |
| Penetration inhibition ratio (%) immediately after treatment | | 66.0 | 65.3 | 60.3 | 57.6 | 55.6 | 56.5 |
| Penetration inhibition ratio (%) after one-month immersion in saliva | | 84.3 | 78.1 | 77.5 | 76.8 | 72.0 | 74.2 |
| | Increase of penetration inhibition ratio | 18.3 | 12.8 | 17.2 | 19.2 | 16.4 | 17.7 |
| | Storage stability | A | A | A | A | A | A |

| | | Raw materials | Example 80 | Example 81 | Example 82 | Example 83 | Example 84 | Example 85 |
|---|---|---|---|---|---|---|---|---|
| Apatite particles (A) | | Hydroxyapatite (D50: 40 nm) (part(s) by weight) | | | | | 35 | |
| | | Hydroxyapatite (D50: 150 nm) (part(s) by weight) | 5 | 2.5 | 0.9 | 2.5 | | |
| | | Hydroxyapatite (D50: 400 nm) (part(s) by weight) | | | | | | 35 |
| Filler (B) | b2 | DCPA (D50: 0.5 μm) (part(s) by weight) | | | | | | |
| | b2 | DCPA (D50: 1 μm) (part(s) by weight) | | | | | | |
| | b2 | DCPA (D50: 2 μm) (part(s) by weight) | 5 | 7.5 | 9.1 | 2.5 | 35 | 35 |
| | b2 | DCPA (D50: 8 μm) (part(s) by weight) | | | | | | |
| | b1 | TTCP (D50: 2 μm) (part(s) by weight) | | | | | | |
| | b1 | Hydroxyapatite (D50: 2 μm) (part(s) by weight) | | | | | | |
| | b2 | α-TCP (D50: 2 μm) (part(s) by weight) | | | | | | |
| | b3 | Calcium carbonate (D50: 2 μm) (part(s) by weight) | | | | | | |
| | b3 | Calcium hydroxide (D50: 2 μm) (part(s) by weight) | | | | | | |
| | b3 | Calcium silicate (D50: 2 μm) (part(s) by weight) | | | | | | |
| | b4 | Ba glass (D50: 2 μm) (part(s) by weight) | | | | | | |
| | b4 | FAS glass (D50: 2 μm) (part(s) by weight) | | | | | | |
| | b4 | Zirconia (D50: 2 μm) (part(s) by weight) | | | | | | |
| | b' | Melamine resin (D50: 2 μm) (part(s) by weight) | | | | | | |
| Fluorine compound | | NaF (part(s) by weight) | | | | | | |
| Thickener | | Ar-130 (part(s) by weight) | | | | | | |
| | | Ar-380 (part(s) by weight) | 5 | 5 | 5 | 5 | | |
| Dispersant (C) | | MACROGOL 400 (part(s) by weight) | 25 | 25 | 25 | 25 | | |
| | | MACROGOL 4000 (part(s) by weight) | 12.5 | 12.5 | 12.5 | 15 | | |
| | | Glycerol (part(s) by weight) | | | | | | |
| | | Water (part(s) by weight) | 47.5 | 47.5 | 47.5 | 50 | 30 | 30 |
| | | Total (part(s) by weight) | 100 | 100 | 100 | 100 | 100 | 100 |
| | | A/B | 1 | 0.33 | 0.1 | 1 | 1 | 1 |
| (A + B + C) relative to 100 parts by weight of dentinal tubule sealant (part(s) by weight) | | | 95 | 95 | 95 | 95 | 100 | 100 |

TABLE 5-continued

|  | | | | | | |
|---|---|---|---|---|---|---|
| C relative to 100 parts by weight of dentinal tubule sealant (part(s) by weight) | 85 | 85 | 85 | 90 | 30 | 30 |
| Operability | A | A | A | A | B | B |
| Initial dentinal tubule sealing ratio (%) | 60.0 | 55.6 | 55.5 | 50.1 | 66.4 | 64.2 |
| Dentinal tubule sealing ratio (%) after one-month immersion in saliva | 83.9 | 74.1 | 71.9 | 62.3 | 89.3 | 84.5 |
| Increase of sealing ratio | 23.9 | 18.5 | 16.4 | 12.2 | 22.9 | 20.3 |
| Penetration inhibition ratio (%) immediately after treatment | 60.0 | 55.6 | 55.5 | 50.1 | 66.4 | 64.2 |
| Penetration inhibition ratio (%) after one-month immersion in saliva | 83.9 | 74.1 | 71.9 | 62.3 | 89.3 | 84.5 |
| Increase of penetration inhibition ratio | 23.9 | 18.5 | 16.4 | 12.2 | 22.9 | 20.3 |
| Storage stability | A | A | A | A | A | A |

TABLE 6

| | Raw materials | Example 86 | Example 87 | Example 88 | Example 89 | Example 90 | Example 91 |
|---|---|---|---|---|---|---|---|
| Apatite particles (A) | Hydroxyapatite (D50: 40 nm) (part(s) by weight) | 5 | | | | | |
| | Hydroxyapatite (D50: 150 nm) (part(s) by weight) | | | 35 | 35 | 5 | 5 |
| | Hydroxyapatite (D50: 400 nm) (part(s) by weight) | | 5 | | | | |
| Filler (B) b2 | DCPA (D50: 0.5 μm) (part(s) by weight) | | | | | | |
| b2 | DCPA (D50: 1 μm) (part(s) by weight) | | | 35 | | 5 | |
| b2 | DCPA (D50: 2 μm) (part(s) by weight) | 5 | 5 | | | | |
| b2 | DCPA (D50: 8 μm) (part(s) by weight) | | | | 35 | | 5 |
| b1 | TTCP (D50: 2 μm) (part(s) by weight) | | | | | | |
| b1 | Hydroxyapatite (D50: 2 μm) (part(s) by weight) | | | | | | |
| b2 | α-TCP (D50: 2 μm) (part(s) by weight) | | | | | | |
| b3 | Calcium carbonate (D50: 2 μm) (part(s) by weight) | | | | | | |
| b3 | Calcium hydroxide (D50: 2 μm) (part(s) by weight) | | | | | | |
| b3 | Calcium silicate (D50: 2 μm) (part(s) by weight) | | | | | | |
| b4 | Ba glass (D50: 2 μm) (part(s) by weight) | | | | | | |
| b4 | FAS glass (D50: 2 μm) (part(s) by weight) | | | | | | |
| b4 | Zirconia (D50: 2 μm) (part(s) by weight) | | | | | | |
| b' | Melamine resin (D50: 2 μm) (part(s) by weight) | | | | | | |
| Fluorine compound | NaF (part(s) by weight) | | | | | | |
| Thickener | Ar-130 (part(s) by weight) | | | | | | |
| | Ar-380 (part(s) by weight) | 5 | 5 | | | 5 | 5 |
| Dispersant (C) | MACROGOL 400 (part(s) by weight) | 25 | 25 | | | 25 | 25 |
| | MACROGOL 4000 (part(s) by weight) | 13 | 12.5 | | | 12.5 | 12.5 |
| | Glycerol (part(s) by weight) | | | | | | |
| | Water (part(s) by weight) | 47.5 | 47.5 | 30 | 30 | 47.5 | 47.5 |
| | Total (part(s) by weight) | 100 | 100 | 100 | 100 | 100 | 100 |
| | A/B | 1 | 1 | 1 | 1 | 1 | 1 |
| (A + B + C) relative to 100 parts by weight of dentinal tubule sealant (part(s) by weight) | | 95 | 95 | 100 | 100 | 95 | 95 |
| C relative to 100 parts by weight of dentinal tubule sealant (part(s) by weight) | | 85 | 85 | 30 | 30 | 85 | 85 |
| | Operability | A | A | B | B | A | A |
| | Initial dentinal tubule sealing ratio (%) | 55.9 | 57.4 | 64.4 | 57.8 | 55.6 | 55.8 |
| | Dentinal tubule sealing ratio (%) after one-month immersion in saliva | 75.2 | 75.5 | 84.1 | 75.7 | 74.8 | 74.4 |
| | Increase of sealing ratio | 19.3 | 18.1 | 19.7 | 17.9 | 19.2 | 18.6 |
| | Penetration inhibition ratio (%) immediately after treatment | 55.9 | 57.4 | 64.4 | 57.8 | 55.6 | 55.8 |

TABLE 6-continued

| | | | | | | | |
|---|---|---|---|---|---|---|---|
| Penetration inhibition ratio (%) after one-month immersion in saliva | | 75.2 | 75.5 | 84.1 | 75.7 | 74.8 | 74.4 |
| Increase of penetration inhibition ratio | | 19.3 | 18.1 | 19.7 | 17.9 | 19.2 | 18.6 |
| Storage stability | | A | A | A | A | A | A |

| | Raw materials | Example 92 | Example 93 | Example 94 | Example 95 | Example 96 | Example 97 |
|---|---|---|---|---|---|---|---|
| Apatite particles (A) | Hydroxyapatite (D50: 40 nm) (part(s) by weight) | | | | | | |
| | Hydroxyapatite (D50: 150 nm) (part(s) by weight) | 35 | 5 | 35 | 5 | 35 | 5 |
| | Hydroxyapatite (D50: 400 nm) (part(s) by weight) | | | | | | |
| Filler (B) b2 | DCPA (D50: 0.5 μm) (part(s) by weight) | | | | | | |
| b2 | DCPA (D50: 1 μm) (part(s) by weight) | | | | | | |
| b2 | DCPA (D50: 2 μm) (part(s) by weight) | | | | | | |
| b2 | DCPA (D50: 8 μm) (part(s) by weight) | | | | | | |
| b1 | TTCP (D50: 2 μm) (part(s) by weight) | 35 | 5 | | | | |
| b1 | Hydroxyapatite (D50: 2 μm) (part(s) by weight) | | | | | | |
| b2 | α-TCP (D50: 2 μm) (part(s) by weight) | | | 35 | 5 | | |
| b3 | Calcium carbonate (D50: 2 μm) (part(s) by weight) | | | | | 35 | 5 |
| b3 | Calcium hydroxide (D50: 2 μm) (part(s) by weight) | | | | | | |
| b3 | Calcium silicate (D50: 2 μm) (part(s) by weight) | | | | | | |
| b4 | Ba glass (D50: 2 μm) (part(s) by weight) | | | | | | |
| b4 | FAS glass (D50: 2 μm) (part(s) by weight) | | | | | | |
| b4 | Zirconia (D50: 2 μm) (part(s) by weight) | | | | | | |
| b' | Melamine resin (D50: 2 μm) (part(s) by weight) | | | | | | |
| Fluorine compound | NaF (part(s) by weight) | | | | | | |
| Thickener | Ar-130 (part(s) by weight) | | | | | | |
| | Ar-380 (part(s) by weight) | | 5 | | 5 | | 5 |
| Dispersant (C) | ACROGOL 400 (part(s) by weight) | | 25 | | 25 | | 25 |
| | MACROGOL 4000 (part(s) by weight) | | 12.5 | | 12.5 | | 12.5 |
| | Glycerol (part(s) by weight) | | | | | | |
| | Water (part(s) by weight) | 30 | 47.5 | 30 | 47.5 | 30 | 47.5 |
| | Total (part(s) by weight) | 100 | 100 | 100 | 100 | 100 | 100 |
| | A/B | 1 | 1 | 1 | 1 | 1 | 1 |
| | (A + B + C) relative to 100 parts by weight of dentinal tubule sealant (part(s) by weight) | 100 | 95 | 100 | 95 | 100 | 95 |
| | C relative to 100 parts by weight of dentinal tubule sealant (part(s) by weight) | 30 | 85 | 30 | 85 | 30 | 85 |
| | Operability | B | A | B | A | B | A |
| | Initial dentinal tubule sealing ratio (%) | 66.5 | 59.9 | 67.8 | 57.7 | 69.3 | 60.2 |
| | Dentinal tubule sealing ratio (%) after one-month immersion in saliva | 92.3 | 84.6 | 91.4 | 81.1 | 92.2 | 84.0 |
| | Increase of sealing ratio | 25.8 | 24.7 | 23.6 | 23.4 | 22.9 | 23.8 |
| | Penetration inhibition ratio (%) immediately after treatment | 66.5 | 59.9 | 67.8 | 57.7 | 69.3 | 60.2 |
| | Penetration inhibition ratio (%) after one-month immersion in saliva | 92.3 | 84.6 | 91.4 | 81.1 | 92.2 | 84.0 |
| | Increase of penetration inhibition ratio | 25.8 | 24.7 | 23.6 | 23.4 | 22.9 | 23.8 |
| | Storage stability | A | A | A | A | A | A |

| | Raw materials | Example 98 | Example 99 | Example 100 | Example 101 | Example 102 | Example 103 |
|---|---|---|---|---|---|---|---|
| Apatite particles (A) | Hydroxyapatite (D50: 40 nm) (part(s) by weight) | | | | | | |
| | Hydroxyapatite (D50: 150 nm) (part(s) by weight) | 35 | 5 | 35 | 5 | 35 | 5 |
| | Hydroxyapatite (D50: 400 nm) (part(s) by weight) | | | | | | |

TABLE 6-continued

| | | | | | | | |
|---|---|---|---|---|---|---|---|
| Filler b2 (B) | DCPA (D50: 0.5 μm) (part(s) by weight) | | | | | | |
| b2 | DCPA (D50: 1 μm) (part(s) by weight) | | | | | | |
| b2 | DCPA (D50: 2 μm) (part(s) by weight) | | | | | | |
| b2 | DCPA (D50: 8 μm) (part(s) by weight) | | | | | | |
| b1 | TTCP (D50: 2 μm) (part(s) by weight) | | | | | | |
| b1 | Hydroxyapatite (D50: 2 μm) (part(s) by weight) | | | | | | |
| b2 | α-TCP (D50: 2 μm) (part(s) by weight) | | | | | | |
| b3 | Calcium carbonate (D50: 2 μm) (part(s) by weight) | | | | | | |
| b3 | Calcium hydroxide (D50: 2 μm) (part(s) by weight) | | | | | | |
| b3 | Calcium silicate (D50: 2 μm) (part(s) by weight) | | | | | | |
| b4 | Ba glass (D50: 2 μm) (part(s) by weight) | | | 35 | 5 | | |
| b4 | FAS glass (D50: 2 μm) (part(s) by weight) | 35 | 5 | | | | |
| b4 | Zirconia (D50: 2 μm) (part(s) by weight) | | | | | | |
| b' | Melamine resin (D50: 2 μm) (part(s) by weight) | | | | | 35 | 5 |
| Fluorine compound | NaF (part(s) by weight) | | | | | | |
| Thickener | Ar-130 (part(s) by weight) | | | | | | |
| | Ar-380 (part(s) by weight) | | 5 | | 5 | | 5 |
| Dispersant (C) | MACROGOL 400 (part(s) by weight) | | 25 | | 25 | | 25 |
| | MACROGOL 4000 (part(s) by weight) | | 12.5 | | 12.5 | | 12.5 |
| | Glycerol (part(s) by weight) | | | | | | |
| | Water (part(s) by weight) | 30 | 47.5 | 30 | 47.5 | 30 | 47.5 |
| | Total (part(s) by weight) | 100 | 100 | 100 | 100 | 100 | 100 |
| | A/B | 1 | 1 | 1 | 1 | 1 | 1 |
| | (A + B + C) relative to 100 parts by weight of dentinal tubule sealant (part(s) by weight) | 100 | 95 | 100 | 95 | 100 | 95 |
| | C relative to 100 parts by weight of dentinal tubule sealant (part(s) by weight) | 30 | 85 | 30 | 85 | 30 | 85 |
| | Operability | B | A | B | A | B | A |
| | Initial dentinal tubule sealing ratio (%) | 63.1 | 56.9 | 64.2 | 55.2 | 64.2 | 57.3 |
| | Dentinal tubule sealing ratio (%) after one-month immersion in saliva | 88.8 | 79.9 | 87.3 | 77.9 | 69.1 | 61.1 |
| | Increase of sealing ratio | 25.7 | 23.0 | 23.1 | 22.7 | 4.9 | 3.8 |
| | Penetration inhibition ratio (%) immediately after treatment | 63.1 | 56.9 | 64.2 | 55.2 | 64.2 | 57.3 |
| | Penetration inhibition ratio (%) after one-month immersion in saliva | 88.8 | 79.9 | 87.3 | 77.9 | 69.1 | 61.1 |
| | Increase of penetration inhibition ratio | 25.7 | 23.0 | 23.1 | 22.7 | 4.9 | 3.8 |
| | Storage stability | A | A | A | A | A | A |

TABLE 7

| | Raw materials | Comparative Example 1 | Comparative Example 2 | Comparative Example 3 | Comparative Example 4 | Comparative Example 5 | Comparative Example 6 | Comparative Example 7 | Comparative Example 8 |
|---|---|---|---|---|---|---|---|---|---|
| Apatite particles (A) | Hydroxyapatite (D50: 40 nm) (part(s) by weight) | | | | | | | | |
| | Hydroxyapatite (D50: 150 nm) (part(s) by weight) | | | 35 | 35 | | | 5 | 5 |
| Filler (B) | b2 DCPA (D50: 0.5 μm) (part(s) by weight) | | | | 35 | | | | 5 |
| b2 | DCPA (D50: 1 μm) (part(s) by weight) | | | | | | | | |
| b2 | DCPA (D50: 2 μm) (part(s) by weight) | 35 | 35 | | | 5 | 5 | | |
| b2 | DCPA (D50: 8 μm) (part(s) by weight) | | | | | | | | |

TABLE 7-continued

| | Raw materials | | | | | | | | |
|---|---|---|---|---|---|---|---|---|---|
| | b2 DCPA (D50: 20 μm) (part(s) by weight) | | 35 | | | | 5 | | |
| | b1 Hydroxyapatite (D50: 2 μm) (part(s) by weight) | 35 | | | | 5 | | | |
| | b1 Hydroxyapatite (D50: 10 μm) (part(s) by weight) | | 35 | | | | 5 | | |
| | b2 α-TCP (D50: 2 μm) (part(s) by weight) | | | | | | | | |
| | b3 Calcium carbonate (D50: 2 μm) (part(s) by weight) | | | | | | | | |
| | b3 Calcium hydroxide (D50: 2 μm) (part(s) by weight) | | | | | | | | |
| | Disodium hydrogen phosphate (part(s) by weight) | | | | | | | | |
| Fluorine compound | NaF (part(s) by weight) | 0.2 | 0.2 | | 0.2 | | 0.2 | | |
| Thickener | Ar-130 (part(s) by weight) | | | | | | | | |
| | Ar-380 (part(s) by weight) | | | | | 5 | 5 | 5 | 5 |
| Dispersant (C) | MACROGOL 400 (part(s) by weight) | | | | | 25 | 25 | 25 | 25 |
| | MACROGOL 4000 (part(s) by weight) | | | | | 10 | 10 | 10 | 10 |
| | Glycerol (part(s) by weight) | 29.8 | 30 | 29.8 | 30 | 49.8 | 50 | 49.8 | 50 |
| | Water (part(s) by weight) | | | | | | | | |
| | Total (part(s) by weight) | 100 | 100 | 100 | 100 | 100 | 100 | 100 | 100 |
| | A/B | 0 | 0 | 1 | 1 | 0 | 0 | 1 | 1 |
| | (A + B + C) relative to 100 parts by weight of dentinal tubule sealant (part(s) by weight) | 99.8 | 100 | 99.8 | 100 | 94.8 | 95 | 94.8 | 95 |
| | C relative to 100 parts by weight of dentinal tubule sealant (part(s) by weight) | 29.8 | 30 | 29.8 | 30 | 84.8 | 85 | 84.8 | 85 |
| | Operability | B | B | B | C | A | A | A | A |
| | Initial dentinal tubule sealing ratio (%) | 65.0 | 45.3 | 35.6 | 40.3 | 55.6 | 33.5 | 25.9 | 38.6 |
| | Dentinal tubule sealing ratio (%) after one-month immersion in saliva | 60.1 | 23.5 | 21.2 | 29.5 | 43.6 | 19.6 | 15.4 | 27.4 |
| | Increase of sealing ratio | −4.9 | −21.8 | −14.4 | −10.8 | −12.0 | −13.9 | −10.5 | −11.2 |
| | Penetration inhibition ratio (%) immediately after treatment | 65.0 | 45.3 | 35.6 | 40.3 | 55.6 | 33.5 | 25.9 | 38.6 |
| | Penetration inhibition ratio (%) after one-month immersion in saliva | 60.1 | 23.5 | 21.2 | 29.5 | 43.6 | 19.6 | 15.4 | 27.4 |
| | Increase of penetration inhibition ratio | −4.9 | −21.8 | −14.4 | −10.8 | −12.0 | −13.9 | −10.5 | −11.2 |
| | Storage stability | A | A | A | A | A | A | A | A |

| | Raw materials | Comparative Example 9 | Comparative Example 10 | Comparative Example 11 | Comparative Example 12 | Comparative Example 13 | Comparative Example 14 | Comparative Example 15 |
|---|---|---|---|---|---|---|---|---|
| Apatite particles (A) | Hydroxyapatite (D50: 40 nm) (part(s) by weight) | | | | 5 | 10 | | |
| | Hydroxyapatite (D50: 150 nm) (part(s) by weight) | 5 | | | | | | |
| Filler (B) | b2 DCPA (D50: 0.5 μm) (part(s) by weight) | | | | | | | |
| | b2 DCPA (D50: 1 μm) (part(s) by weight) | | | | | | 9.8 | 40.5 |
| | b2 DCPA (D50: 2 μm) (part(s) by weight) | 5 | 20 | | | | | |
| | b2 DCPA (D50: 8 μm) (part(s) by weight) | | | | | | | |
| | b2 DCPA (D50: 20 μm) (part(s) by weight) | | | | | | | |
| | b1 Hydroxyapatite (D50: 2 μm) (part(s) by weight) | | 10 | 17 | | | | |
| | b1 Hydroxyapatite (D50: 10 μm) (part(s) by weight) | | | | | | | |
| | b2 α-TCP (D50: 2 μm) (part(s) by weight) | | | 17 | | | | |
| | b3 Calcium carbonate (D50: 2 μm) (part(s) by weight) | | | | | | 26.2 | |
| | b3 Calcium hydroxide (D50: 2 μm) (part(s) by weight) | | | | | | | 0.5 |

TABLE 7-continued

| | | | | | | | | |
|---|---|---|---|---|---|---|---|---|
| | Disodium hydrogen phosphate (part(s) by weight) | | | | | | 5 | 4 |
| Fluorine compound | NaF (part(s) by weight) | | | | | | | 0.2 |
| Thickener | Ar-130 (part(s) by weight) | | | | | | 3.5 | 4 |
| | Ar-380 (part(s) by weight) | 20 | | | | | | |
| Dispersant (C) | MACROGOL 400 (part(s) by weight) | 15 | 10 | 8 | | | 10.0 | 5.4 |
| | MACROGOL 4000 (part(s) by weight) | 5 | 10 | 8 | | | 2.9 | 3 |
| | Glycerol (part(s) by weight) | 50 | 20 | 20 | 95 | 90 | 18.9 | 13.9 |
| | Water (part(s) by weight) | | 30 | 30 | | | 23.7 | 28.5 |
| | Total (part(s) by weight) | 100 | 100 | 100 | 100 | 100 | 100 | 100 |
| | A/B | 1 | 0 | 0 | — | — | 0 | 0 |
| | (A + B + C) relative to 100 parts by weight of dentinal tubule sealant (part(s) by weight) | 80 | 100 | 100 | 100 | 100 | 91.5 | 91.8 |
| | C relative to 100 parts by weight of dentinal tubule sealant (parl(s) by weight) | 70 | 70 | 66 | 95 | 90 | 55.5 | 50.8 |
| | Operability | C | A | A | A | A | A | A |
| | Initial dentinal tubule sealing ratio (%) | 35.6 | 40.2 | 39.5 | 15.1 | 19.5 | 65.8 | 62.3 |
| | Dentinal tubule sealing ratio (%) after one-month immersion in saliva | 36.5 | 30.2 | 31.2 | 9.4 | 15.5 | 80.2 | 74.2 |
| | Increase of sealing ratio | 0.9 | −10.0 | −8.3 | −5.7 | −4.0 | 14.4 | 11.9 |
| | Penetration inhibition ratio (%) immediately after treatment | 36.9 | 40.2 | 39.5 | 15.1 | 19.5 | 65.8 | 62.3 |
| | Penetration inhibition ratio (%) after one-month immersion in saliva | 38.9 | 30.2 | 31.2 | 9.4 | 15.5 | 80.2 | 74.2 |
| | Increase of penetration inhibition ratio | 2.0 | −10.0 | −8.3 | −5.7 | −4.0 | 14.4 | 11.9 |
| | Storage stability | A | A | A | A | A | B | B |

The invention claimed is:

1. A dentinal tubule sealant, comprising:
(A) apatite particles (A) having an average particle diameter of 500 nm or less;
(B) a filler (B) having an average particle diameter of 1 to 10 μm; and
(C) a dispersant (C),
wherein the dentinal tubule sealant comprises 0 to 20 parts by weight of water, relative to 100 parts by weight of the dentinal tubule sealant,
wherein:
a weight ratio (A/B) of the apatite particles (A) to the filler (B) is 0.05 to 15;
the dentinal tubule sealant comprises 15 to 95 parts by weight of the dispersant (C) relative to 100 parts by weight in total of the apatite particles (A) and the filler (B);
a total amount of the apatite particles (A), the filler (B), and the dispersant (C) is 85 parts by weight or more relative to 100 parts by weight of the dentinal tubule sealant;
the filler (B) is an inorganic filler (b) comprising a mixture of basic calcium phosphate particles (b1), poorly-soluble calcium phosphate particles (b2) and a phosphorus-free calcium compound (b3), wherein a Ca/P ratio of the sum of (b1), (b2) and (b3) is 1.7 to 2.8;
the basic calcium phosphate particles (b1) comprise at least one member selected from the group consisting of tetracalcium phosphate ($Ca_4(PO_4)_2O$) particles and apatite particles;
the poorly-soluble calcium phosphate particles (b2) comprise at least one member selected from the group consisting of anhydrous calcium monohydrogen phosphate ($CaHPO_4$) particles and tricalcium phosphate ($Ca_3(PO_4)_2$) particles; and
the phosphorus-free calcium compound (b3) is at least one member selected from the group consisting of calcium hydroxide ($Ca(OH)_2$) and calcium carbonate ($CaCO_3$).

2. The dentinal tubule sealant according to claim 1, wherein the inorganic filler (b) further comprises an inorganic filler (b4) other than (bp to (b3).

3. The dentinal tubule sealant according to claim 1, wherein the dispersant (C) is water, a nonaqueous liquid, or both.

4. The dentinal tubule sealant according to claim 3, wherein the dispersant (C) comprises at least one nonaqueous liquid selected from the group consisting of a polyether, a monohydric alcohol, and a polyhydric alcohol.

5. The dentinal tubule sealant according to claim 1, wherein the basic calcium phosphate particles (b1) comprise tetracalcium phosphate ($Ca_4(PO_4)_2O$) particles.

6. The dentinal tubule sealant according to claim 1, wherein the basic calcium phosphate particles (b1) comprise apatite particles.

7. The dentinal tubule sealant according to claim 1, wherein the poorly-soluble calcium phosphate particles (b2) comprise anhydrous calcium monohydrogen phosphate ($CaHPO_4$) particles.

8. The dentinal tubule sealant according to claim 1, wherein the poorly-soluble calcium phosphate particles (b2) comprise tricalcium phosphate ($Ca_3(PO_4)_2$) particles.

9. The dentinal tubule sealant according to claim 1, wherein the phosphorus-free calcium compound (b3) comprises calcium hydroxide ($Ca(OH)_2$).

10. The dentinal tubule sealant according to claim 1, the phosphorus-free calcium compound (b3) comprises calcium carbonate ($CaCO_3$).

11. The dentinal tubule sealant according to claim 1, which is a one-component-type dentinal tubule sealant.

12. The dentinal tubule sealant according to claim 2, wherein the inorganic filler (b4) comprises at least one member selected from the group consisting of quartz, silica, alumina, zirconia, titania, silica-titania, silica-titania-barium oxide, silica-zirconia, silica-alumina, lanthanum glass, borosilicate glass, soda glass, barium glass, strontium glass, glass ceramics, aluminosilicate glass, barium boroaluminosilicate glass, strontium boroaluminosilicate glass, fluoroaluminosilicate glass, calcium fluoroaluminosilicate glass, strontium fluoroaluminosilicate glass, barium fluoroaluminosilicate glass, and strontium calcium fluoroaluminosilicate glass.

13. The dentinal tubule sealant according to claim 2, wherein the inorganic filler (b4) comprises at least one member selected from the group consisting of barium glass, fluoroaluminosilicate glass, silica, and zirconia.

14. The dentinal tubule sealant according to claim 1, wherein the dispersant (C) comprises at least one nonaqueous liquid selected from the group consisting of polyethylene glycol, polypropylene glycol, ethanol, methanol, glycerol, ethylene glycol, propylene glycol, and diglycerol.

15. The dentinal tubule sealant according to claim 1, wherein the dispersant (C) comprises water.

16. The dentinal tubule sealant according to claim 1, wherein the dispersant (C) comprises at least one member selected from the group consisting of glycerol and polyethylene glycol.

17. The dentinal tubule sealant according to claim 1, which contains 15 to 95 parts by weight of the dispersant (C) relative to 100 parts by weight in total of the apatite particles (A) and the filler (B).

18. The dentinal tubule sealant according to claim 1, wherein the total amount of the apatite particles (A), the filler (B), and the dispersant (C) is 85 parts by weight or more relative to 100 parts by weight of the dentinal tubule sealant.

19. A method of preparing the dentinal tubule sealant according to claim 1, comprising combining (A), (B) and (C).

20. A method of sealing a dentinal tubule, comprising applying the dentinal tubule according to claim 1 to the dentin of teeth.

* * * * *